(12) United States Patent
Severinov et al.

(10) Patent No.: US 7,442,762 B2
(45) Date of Patent: Oct. 28, 2008

(54) MUTATIONAL DERIVATIVES OF MICROCIN J25

(75) Inventors: Konstantin Severinov, Piscataway, NJ (US); Richard Ebright, North Brunswick, NJ (US); Olga Pavlova, Moscow (RU); Elena Sineva, Galveston, TX (US)

(73) Assignee: Rutgers, The State University of New Jersey, New Brunswick, NY (US)

( * ) Notice: Subject to any disclaimer, the term of this patent is extended or adjusted under 35 U.S.C. 154(b) by 0 days.

(21) Appl. No.: 11/371,736

(22) Filed: Mar. 9, 2006

(65) Prior Publication Data

US 2008/0200374 A1 Aug. 21, 2008

Related U.S. Application Data

(60) Provisional application No. 60/659,440, filed on Mar. 9, 2005.

(51) Int. Cl.
*C07K 14/00* (2006.01)
*C07K 14/195* (2006.01)
*C12Q 1/04* (2006.01)
*C12Q 1/37* (2006.01)

(52) U.S. Cl. .......................... 530/326; 530/300; 435/34

(58) Field of Classification Search ........................ None
See application file for complete search history.

(56) References Cited

U.S. PATENT DOCUMENTS

| | | |
|---|---|---|
| 6,225,076 B1 | 5/2001 | Darst et al. |
| 2002/0034808 A1 | 3/2002 | Darst et al. |
| 2003/0003481 A1 | 1/2003 | Landick et al. |
| 2003/0232369 A1 | 12/2003 | Bushnell et al. |

FOREIGN PATENT DOCUMENTS

WO WO 2004/023093 * 3/2004

OTHER PUBLICATIONS

Kim et al.; Mechanism of ATP-Dependent Promoter Melting by Transcription Factor IIH; Science; vol. 288, No. 5470; pp. 1418-1421; May 26, 2000.
Stuart B. Levy; The Challenge of Antibiotic Resistance; Scientific American; vol. 278, No. 3; pp. 46-53; Mar. 1998.
Ravigllone, et al.; The Burden of Drug-Resistant Tuberculosis and Mechanisms for Its Control; Annals New York Academy of Sciences; vol. 953;pp. 88-97; (2001).
McLafferty, et al.; M13 Bacteriophage Displaying Disulfide-Constrained Microproteins; Gene, 128 ; pp. 29-36; (1993).
Luzzago, et al; Mimicking of Discontinuous Epitopes by Phage-Displayed Peptides, I. Epitope Mapping of Human H Ferritin Using A Phage Library of Constrained Peptides; Gene, 128; pp. 51-57; (1993).
Cwirla, et al; Peptides on Phage: A Vast Library of Peptides for Identifying Ligands; Proceedings of the National Academy of Sciences; vol. 87, No. 16; pp. 6378-6382; Aug. 1990.
Devlin, et al; Random Peptide Libraries: A Source of Specific Protein Binding Molecules; Science; vol. 249; pp. 404-406; Jul. 27, 1990.
Perez-Paya, et al; Soluble Combinatorial Libraries of Organic, Peptidomimetic and Peptide Diversities; Trends in Analytical Chemistry; vol. 14, No. 2; pp. 83-92; (1995).
Pinilla, et al; Versatility of Positional Scanning Synthetic Combinatorial Libraries for the Identification of Individual Compounds; Drug Development Research 33; pp. 133-145; (1994).
Gallop, et al; Applications of Combinatorial Technologies to Drug Discovery. 1. Background and Peptide Combinatorial Libraries; Journal of Medicinal Chemistry; vol. 37, No. 9; pp. 1233-1251; Apr. 29, 1994.
Geysen, et al.; The Delineation of Peptides Able to Mimic Assembled Epitopes; pp. 130-149.
Richard A. Houghten; General Method for the Rapid Solid-Phase Synthesis of Large Numbers of Peptides: Specificity of Antigen-Antibody Interaction At the Level of Individual Amino Acids; Proc. Natl. Acad. Sci. USA; vol. 82; pp. 5131-5135; Aug. 1985 Immunology.
Richard H. Ebright; RNA Polymerase: Structural Similarities Between Bacterial RNA Polymerase and Eukaryotic RNA Polymerase II; J. Mol. Biol.; vol. 304, No. 5; pp. 687-698; (2000).
Pinilla, et al.; A Review of the Utility of Soluble Peptide Combinatorial Libraries; Biopolymers (Peptide Science); vol. 37; pp. 221-240; (1995).
Houghten, et al.; The Use of Synthetic Peptide Combinatorial Libraries for the Identification of Bioactive Peptides; BioTechniques; vol. 13, No. 3; pp. 412-421; (1992).
Ostresh, et al.; Libraries from Libraries: Chemical Transformation of Combinatorial Libraries to Extend the Range and Repertoire of Chemical Diversity; Proc. Natl. Acad. Sci. USA; vol. 91; pp. 11138-11142; Nov. 1994 Chemistry.
Blondelle, et al.; Identification of Antimicrobial Peptides by Using Combinatorial Libraries Made Up of Unnatural Amino Acids; Antimicrobial Agents and Chemotherapy; vol. 38, No. 10; pp. 2280-2286; Oct. 1994.
Pinilla, et al.; Rapid Identification of High Affinity Peptide Ligands Using Positional Scanning Synthetic Peptide Combinatorial Libraries; BioTechniques; vol. 13, No. 6; pp. 901-905; Dec. 1992.
Scott, et al.; Searching for Peptide Ligands With An Epitope Library; Science; vol. 249; pp. 386-390; Jul. 27, 1990.
McConnell, et al.; Constrained Peptide Libraries as a Tool for Finding Mimotopes; Gene; vol. 151, Nos. 1 and 2; pp. 115-118; (1994).
Houghten, et al.; Generation and Use of Synthetic Peptide Combinatorial Libraries for Basic Research and Drug Discovery; Nature; vol. 354, No. 6348; pp. 84-86; Nov. 7, 1991.
Parmley, et al.; Antibody-Selectable Filamentous fd Phage Vectors: Affinity Purification of Target Genes; Gene; vol. 73; pp. 305-318; (1988).

(Continued)

*Primary Examiner*—Anish Gupta
*Assistant Examiner*—Julie Ha
(74) *Attorney, Agent, or Firm*—Hoffman & Baron, LLP

(57) ABSTRACT

Analogs of bacteriocidal peptide microcin J25 (MccJ25) are provided that have an amino acid sequence that differs from that of MccJ25 by having at least one amino acid substitution; and that inhibit bacterial cell growth with a potency at least equal to that of MccJ25.

6 Claims, 10 Drawing Sheets

OTHER PUBLICATIONS

Devlin, et al.; Random Peptide Libraries; A Source of Specific Protein Binding Molecules; Science; vol. 249, No. 4967; pp. 404-406; Jul. 27, 1990.

D. A. Mitchison; Role of Individual Drugs In the Chemotherapy of Tuberculosis; International Journal of Tuberculosis and Lung Disease; 4(9); pp. 796-806; (2000).

N. W. Schluger; The Impact of Drug Resistance on the Global Tuberculosis Epidemic; International Journal of Tuberculosis and Lung Disease; 4(2); pp. 571-575; 2000.

Lam, et al.; A New Type of Synthetic Peptide Library for Identifying Ligand-Binding Activity; Nature; vol. 354, pp. 82-84; Nov. 7, 1991.

Naryshkin, et al.; Structural Organization of the RNA Polymerase-Promoter Open Complex; Cell; vol. 101, No. 6; pp. 601-611; Jun. 9, 2000.

Cramer, et al.; Architecture of RNA Polymerase II and Implications for the Transcription Mechanism; Science; vol. 288, No. 5466; pp. 640-649; Apr. 28, 2000.

Zhou, et al; Identification of the Activating Region of Catabolite Gene Activator Protein (CAP): Isolation and Characterization of Mutants of CAP Specifically Defective In Transcription Activation; Proc. Natl. Acad. Sci. USA; vol. 90; pp. 6081-6085; Jul. 1993 Biochemistry.

Blinder, et al.; Emerging Infectious Diseases: Public Health Issues for the 21st Century; Science; vol. 284, pp. 1311-1313; May 21, 1999.

Christopher Walsh; Molecular Mechanisms That Confer Antibacterial Drug Reisstance; Nature, vol. 406; pp. 775-781; Aug. 17, 2000.

Gill, et al.; Calculation of Protein Extinction Coefficients from Amino Acid Sequence Data; Analytical Biochemistry; vol. 182; pp. 319-326; (1989).

Gill, et al.; *Escherichia coli* s70 and NusA Proteins: I. Binding Interactions With Core RNA Polymerase in Solution and Within the Transcription Complex; J. Mol. Biol.; Vol. 220, No. 2; pp. 307-324; (1991).

Cech, et al.; Characterization of Ribonucleic Acid Polymerase-T7 Promoter Binary Complexes; Biochemistry; vol. 19; pp. 2440-2447; May 27, 1980.

Felici, et al.; Selection of Antibody Ligands from a Large Library of Oligopeptides Expressed on a Multivalent Exposition Vector; J. Mol. Biol.; vol. 222, No. 2; pp. 301-310; (1991).

Ostresh, et al.; Peptide Libraries: Determination of Relative Reaction Rates of Protected Amino Acids in Competitive Couplings; Biopolymers; vol. 34, No. 12; pp. 1681-1689; Dec. 1994.

Blondelle, et al.; The Antimicrobial Activity of Hexapeptides Derived from Synthetic Combinatorial Libraries; Journal of Applied Bacteriology; vol. 78; pp. 39-46; (1995).

Raviglione, et al.; The Burden of Drug-Resistant Tuberculosis and Mechanisms for Its Control; Annals of the New York Academy of Sciences; vol. 953; pp. 88-97; (2001).

Epshtein, et al.; Swing-Gate Model of Nucleotide Entry Into the RNA Polymerase Active Center; Molecular Cell; vol. 10, No. 3; pp. 623-634; Sep. 2002.

Murakami, et al.; Structural Basis of Transcription Initiation: An RNA Polymerase Holoenzyme-DNA Complex; Science; vol. 296; pp. 1285-1290; May 17, 2002.

Mukhopadhyay, et al.; Translocation of σ70 with RNA Polymerase During Transcription: Fluorescence Resonance Energy Transfer Assay for Movement Relative to DNA; Cell; vol. 106; pp. 453-463; Aug. 24, 2001.

Campbell, et al.; Structural Mechanism for Rifampicin Inhibition of Bacterial RNA Polymerase; Cell; vol. 104, No. 6; pp. 901-912; Mar. 23, 2001.

Vassylyev, et al.;Crystal Structure of a bacterial RNA Polymerase Holoenzyme at 2.6 Å Resolution; Nature; pp. 712-719; Jun. 2002.

Gnatt, et al.; Structural Basis of Transcription: An RNA Polymerase II Elongation Complex at 3.3 Å Resolution; Science; vol. 292; pp. 1876-1881; Jun. 8, 2001.

Mekler, et al.; Structural Organization of Bacterial RNA Polymerase Holoenzyme and the RNA Polymerase-Promoter Open Complex; Cell; vol. 108, No. 5; pp. 599-614; Mar. 8, 2002.

Zhang, et al.; Crystal Structure of Thermus Aquaticus Core RNA Polymerase at 3.3 Å Resolution; Cell; vol. 98; pp. 811-824; (1999).

Korzheva, et al.; A Structural Model of Transcription Elongation; Science; vol. 289; pp. 619-625; Jul. 28, 2000.

Wang, et al.; Discontinuous Movements of DNA and RNA in RNA Polymerase Accompany Formation of a Paused Transcription Complex; Cell; vol. 81, No. 3; pp. 341-350; May 5, 1995.

Niu, et al.; Transcription Activation At Class II CAP-Dependent Promoters: Two Interactions Between CAP and RNA Polymerase; Cell; vol. 87, No. 6; pp. 1123-1134; Dec. 13, 1996.

Solbiati, et al.; Genetic Analysis of Plasmid Determinants for Microcin J25 Production and Immunity; Journal of Bacteriology; vol. 178, No. 12; pp. 3661-3663; Jun. 1996.

Solbiati, et al.; Sequence Analysis of the Four Plasmid Genes Required to Produce the Circular Peptide Antibiotic Microcin J25; Journal of Bacteriology; vol. 181, No. 8; pp. 2659-2662; Apr. 1999.

Blond, et al.; The Cyclic Structure of Microcin J25, a 21-Residue Peptide Antibiotic from *Escherichia coli*; Eur. J. Biochem.; vol. 259; pp. 747-755; (1991).

Zhou, et al.; Random Mutagenesis of Gene-sized DNA Molecules by Use of PCR with Taq DNA Polymerase; Nucleic Acids Research; vol. 19, No. 21; p. 6052; (1991).

Ostresh, et al.; Generation and Use of Nonsupport-Bound Peptide and Peptidominetic Combinatorial Libraries; Methods in Enzymology; vol. 267; pp. 220-234; (1996).

Yuzenkova, et al.; Mutations of Bacterial RNA Polymerase Leading to Resistance to Microcin J25; Journal of Biological Chemistry; vol. 277, No. 52; pp. 50867-50875; Dec. 27, 2002.

Christie, et al.; *Escherichia coli* rpoC397 Encodes a Temperature-Sensitive C-Terminal Frameshift in the B' Subunit of RNA Polymerase That Blocks Growth of Bacteriophage P2; Journal of Bacteriology; vol. 178, No. 23; pp. 6991-6993; Dec. 1996.

Bushnell, et al.; Structural Basis of Transcription: x-Amanitin-RNA Polymerase II Cocrystal at 2.8 Å Resolution; PNAS; vol. 99, No. 3; pp. 1218-1222; Feb. 5, 2002.

Delgado, et al.; *Escherichia coli* RNA Polymerase Is the Target of the Cyclopeptide Antibiotic Microcin J25; Journal of Bacteriology; vol. 183, No. 15; pp. 4543-4550; Aug. 2001.

\* cited by examiner

Mature MccJ25 assumes a highly unusual "threaded lasso" fold

A lactam linkage between the first and the eighth MccJ25 amino acids creates a small ring; the tail of the molecule passes through the ring and is topologically trapped. As a result, MccJ25 is extremely stable: it withstands autoclaving without loosing activity.

RNA polymerases resistant to MccJ25 harbor substitutions in the secondary channel

The location of substitutions leading to MccJ25 resistance (red and purple) and structural modeling of MccJ25 (green) interaction with RNAP suggests that the mechanism of transcription inhibition by MccJ25 consists of occlusion of RNAP secondary channel and prevention of substrate traffic to the enzyme's catalytic center (white sphere on the left panel).

Fig. 4

A biological test for mutant *mcjA* activity

Cells producing active
MccJ25 give clearance
zones in top agar

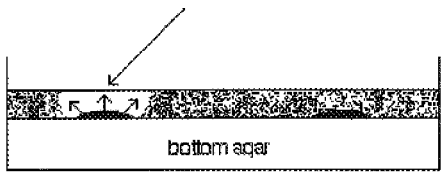

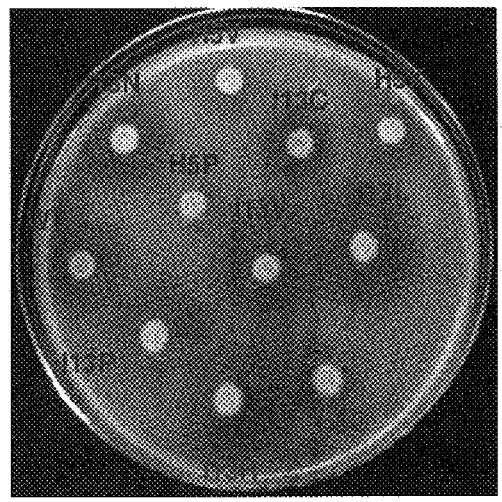

A side view of a Petri dish containing two layers of agar. At the surface of the bottom layer cells harboring *mcj* plasmids are spotted and allowed to grow overnight. The top layer which contains a tester strain is then poured over the bottom layer and development of clearance zones is monitored.

The tester strains used in the two-layer assay include *i)* wt, MccJ25-sensitive *E. coli*; *ii)* mutant, MccJ25-resistant cells with substitutions at various positions of the RNA polymerase secondary channel; *iii)* MccJ25 resistant Gram-positive bacteria.

Fig. 5

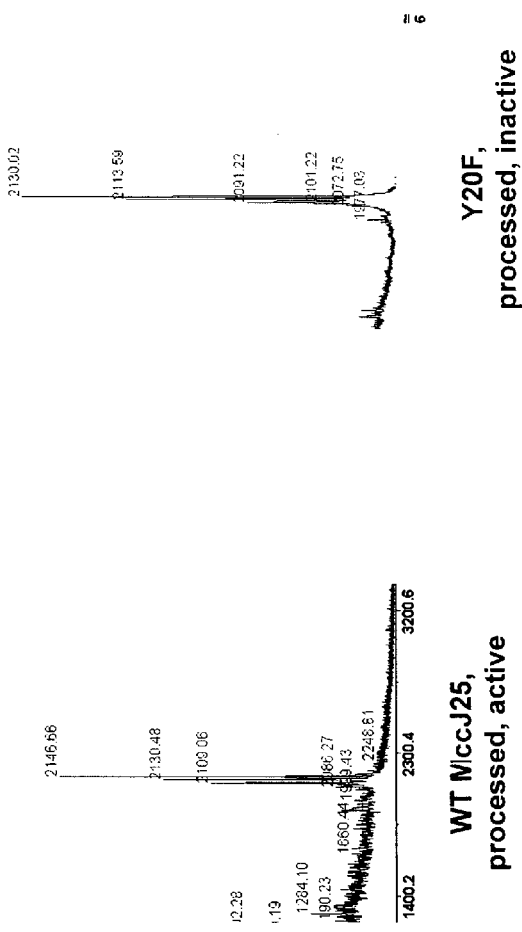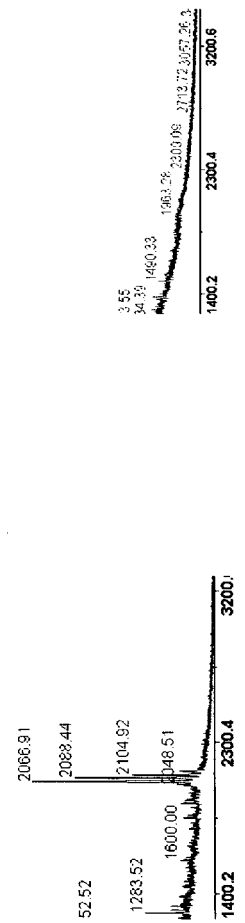
Fig. 9

**Biologically inactive processed MccJ25 mutants are being tested for their ability to inhibit *E. coli* RNA polymerase *in vitro*.**

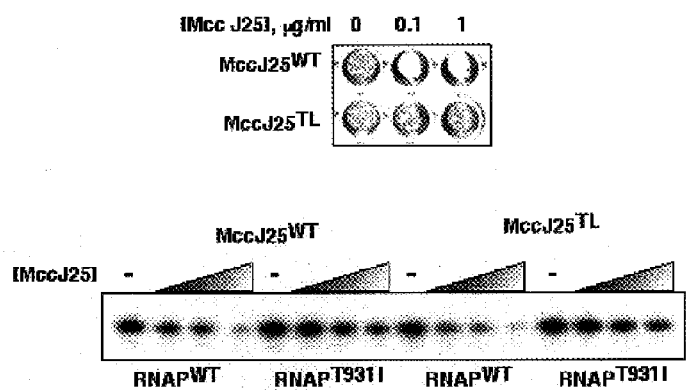

Comparison of wild-type MccJ25 and MccJ25 mutant (MccJ25^TL) which is inactive *in vivo*. At the top, the growth of sensitive *E. coli* cells in microtiter plate wells containing the indicated concentrations of MccJ25 is shown. At the bottom, results of *in vitro* transcription by wild-type RNAP and MccJ25-resistant RNAP harboring the β' T931I mutation in the absence or in the presence of increasing concentrations of wild-type or mutant MccJ25 are shown.

Fig. 10

MUTATIONAL DERIVATIVES OF MICROCIN J25

CROSS-REFERENCE TO RELATED APPLICATIONS

This application claims priority to provisional application No. 60/659,440, filed Mar. 9, 2005, the entire contents of which are incorporated herein by reference.

GOVERNMENT SUPPORT

This invention was supported with U.S. Government funds (NIH R01-GM64530). Therefore, the Government may have rights in the invention.

BACKGROUND INFORMATION

Bacterial infections remain among the most common and deadly causes of human disease. Infectious diseases are the third leading cause of death in the United States and the leading cause of death worldwide (Binder et al. (1999) *Science* 284, 1311-1313). Multi-drug-resistant bacteria now cause infections that pose a grave and growing threat to public health. It has been shown that bacterial pathogens can acquire resistance to first-line and even second-line antibiotics (Stuart B. Levy, The Challenge of Antibiotic Resistance, in Scientific American, 46-53 (March, 1998); Walsh, C. (2000) *Nature* 406, 775-781; Schluger, N. (2000) *Int. J. Tuberculosis Lung Disease* 4, S71-S75; Raviglione et al., (2001) *Ann. NY Acad. Sci.* 953, 88-97). New approaches to drug development are necessary to combat the ever-increasing number of antibiotic-resistant pathogens. The present invention provides one such approach.

RNA polymerase (RNAP) is the molecular machine responsible for transcription and is the target, directly or indirectly, of most regulation of gene expression (Ebright, R. (2000) *J. Mol. Biol.* 304, 687-698; Darst, S. (2001) *Curr. Opin. Structl. Biol.* 11, 155-162; Cramer, P. (2002) *Curr. Opin. Structl. Biol.* 12, 89-97; Murakami & Darst (2003) *Curr. Opin. Structl. Biol.* 13, 31-39; Borukhov & Nudler (2003) *Curr. Opin. Microbiol.* 6, 93-100; Landick, R. (2001) *Cell* 105, 567-570; Korzheva & Mustaev (2001) *Curr. Opin. Microbiol.* 4, 119-125; Armache, et al. (2005) *Curr. Opin. Structl. Biol.* 15, 197-203; Woychik & Hampsey (2002); *Cell* 108, 453-463; Asturias, F. (2004) *Curr. Opin. GenetDev.* 14, 121-129; Cramer, P. (2004) *Curr. Opin. Genet. Dev.* 14, 218-226; Geiduschek & Kassayetis (2001) *J. Mol. Biol.* 310, 1-26). Bacterial RNAP core enzyme has a molecular mass of ~380,000 Da and consists of one $\beta'$ subunit, one $\beta$ subunit, two $\alpha$ subunits, and one c subunit; bacterial RNAP holoenzyme has a molecular mass of ~450,000 Da and consists of bacterial RNAP core enzyme in complex with the transcription initiation factor $\sigma$ (Ebright, R. (2000) *J. Mol. Biol.* 304, 687-698; Darst, S. (2001) *Curr. Opin. Structl. Biol.* 11, 155-162; Cramer, P. (2002) *Curr. Opin. Structl. Biol.* 12, 89-97; Murakami & Darst (2003) *Curr. Opin. Structl. Biol.* 13, 31-39; Borukhov & Nudler (2003) *Curr. Opin. Microbiol.* 6, 93-100). Bacterial RNAP core subunit sequences are conserved across Gram-positive and Gram-negative bacterial species (Ebright, R. (2000) *J. Mol. Biol.* 304, 687-698; Darst, S. (2001) *Curr. Opin. Structl. Biol.* 11, 155-162; Iyer, et al. (2004) *Gene* 335, 73-88). Eukaryotic RNAP I, RNAP II, and RNAP III contain counterparts of all bacterial RNAP core subunits, but eukaryotic-subunit sequences and bacterial-subunit sequences exhibit only limited conservation (Ebright, R. (2000) *J. Mol. Biol.* 304, 687-698; Darst, S. (2001) *Curr. Opin. Structl. Biol.* 11, 155-162; Cramer, P. (2002) *Curr. Opin. Structl. Biol.* 12, 89-97).

Bacterial RNAP is a proven target for antibacterial therapy (Chopra, et al. (2002) *J. Appl. Microbiol.* 92, 4S-15S; Darst, S. (2004) *Trends Biochem. Sci.* 29, 159-162). The suitability of bacterial RNAP as a target for antibacterial therapy follows from the fact that bacterial RNAP is an essential enzyme (permitting efficacy), the fact that bacterial RNAP subunit sequences are conserved (providing a basis for broad-spectrum activity), and the fact that bacterial RNAP subunit sequences are only weakly conserved in eukaryotic RNAP I, RNAP II, and RNAP III (providing a basis for therapeutic selectivity).

The rifamycin antibacterial agents—notably rifampicin, rifapentine, and rifabutin—function by binding to and inhibiting bacterial RNAP (Chopra, et al. (2002) *J. Appl. Microbiol.* 92, 4S-15S; Darst, S. (2004) *Trends Biochem. Sci.* 29, 159-162; Floss & Yu (2005) *Chem. Rev.* 105, 621-632; Campbell, et al. (2001) *Cell* 104, 901-912; Artsimovitch, et al. (2005) *Cell* 122, 351-363). The rifamycins bind to a site on bacterial RNAP adjacent to the RNAP active center and sterically and/or allosterically prevent extension of RNA chains beyond a length of 2-3 nt (Chopra, et al. (2002) *J. Appl. Microbiol.* 92, 4S-15S; Darst, S. (2004) *Trends Biochem. Sci.* 29, 159-162; Floss & Yu (2005) *Chem. Rev.* 105, 621-632; Campbell, et al. (2001) *Cell* 104, 901-912; Artsimovitch, et al. (2005) *Cell* 122, 351-363). The rifamycins are in current clinical use in treatment of Gram-positive and Gram-negative bacterial infections (Chopra, et al. (2002) *J. Appl. Microbiol.* 92, 4S-15S; Darst, S. (2004) *Trends Biochem. Sci.* 29, 159-162; Floss & Yu (2005) *Chem. Rev.* 105, 621-632; Campbell, et al. (2001) *Cell* 104, 901-912; Artsimovitch, et al. (2005) *Cell* 122, 351-363). The rifamycins are of particular importance in treatment of tuberculosis; the rifamycins are first-line anti-tuberculosis agents and are the only anti-tuberculosis agents able rapidly to clear infection and prevent relapse (Mitchison, D. (2000) *Int. J. Tuberc. Lung Dis.* 4, 796-806). The rifamycins also are of importance in treatment of bacterial infections relevant to biowarfare or bioterrorism; combination therapy with ciprofloxacin, clindamycin, and rifampicin was successful in treatment of inhalational anthrax following the 2001 anthrax attacks (Mayer, et al. (2001) *JAMA* 286, 2549-2553), and combination therapy with ciprofloxacin and rifampicin, or doxycycline with rifampicin, is recommended for treatment of future cases of inhalational anthrax (Centers for Disease Control and Prevention (2001) *JAMA* 286, 2226-2232).

The clinical utility of the rifamycin antibacterial agents is threatened by the existence of bacterial strains resistant to rifamycins (Chopra, et al. (2002) *J. Appl. Microbiol.* 92, 4S-15S; Darst, S. (2004) *Trends Biochem. Sci.* 29, 159-162; Floss & Yu (2005) *Chem. Rev.* 105, 621-632; Campbell, et al. (2001) *Cell* 104, 901-912; Artsimovitch, et al. (2005) *Cell* 122, 351-363). Resistance to rifamycins typically involves substitution of residues in or immediately adjacent to the rifamycin binding site on bacterial RNAP—i.e., substitutions that directly decrease binding or function of rifamycins. A significant and increasing percentage of cases of tuberculosis are resistant to rifampicin (1.4% of new cases, 8.7% of previously treated cases, and 100% of cases designated multidrug-resistant, in 1999-2002; Schluger, N. (2000) *Int. J. Tuberc. Lung Dis.* 4, S71-S75; Raviglione, et al. (2001) *Ann. N.Y. Acad. Sci.* 953, 88-97; Zumia, et al. (2001) *Lancet Infect. Dis.* 1, 199-202; Dye, et al. (2002) *J. Infect. Dis.* 185, 1197-1202; WHO/IUATLD (2003) *Anti-tuberculosis drug resistance in the world: third global report* (WHO, Geneva)). Strains of bacterial bioweapons agents resistant to rifampicin can be, and have been, constructed (Lebedeva, et al. (1991) *Antibiot. Khimioter.* 36, 19-22; Pomerantsev, et al. (1993) *Antibiot. Khimioter.* 38, 34-38; Volger, et al. (2002) *Antimicrob. Agents Chemother.* 46, 511-513; Marianelli, et al. (204) *J. Clin. Microbiol.* 42, 5439-5443).

In view of the public-health threat posed by rifamycin-resistant and multidrug-resistant bacterial infections, there is an urgent need for new classes of antibacterial agents that (i) target bacterial RNAP (and thus have the same biochemical effects as rifamycins), but that (ii) target sites within bacterial RNAP distinct from the rifamycin binding site (and thus do not show cross-resistance with rifamycins). (See Chopra, et al. (2002) *J. Appl. Microbiol.* 92, 4S-15S; Darst, S (2004) *Trends Biochem. Sci.* 29, 159-162.)

Recently, crystallographic structures have been determined for bacterial RNAP and eukaryotic RNAP II (Zhang et al., (1999) *Cell* 98, 811-824; Cramer et al., (2000) *Science* 288, 640-649; Naryshkin et al., (2000) *Cell* 101, 601-611; Kim et al., (2000) *Science* 288, 1418-1421; Korzheva et al., (2000) *Science* 289, 619-625; Ebright, R. (2000) *J. Mol. Biol.* 304, 687-689; Cramer et al., (2001) *Science* 292, 1863-1876; Gnatt et al., (2001) *Science* 292, 1876-1882; Mekler et al., (2002) *Cell* 108, 599-614; Murakami et al., (2002) *Science* 296, 1280-1284; Murakami et al., (2002) *Science* 296, 1285-1290; Vassylyev et al., (2002) *Nature* 417, 712-719; Bushnell et al., (2004) *Science* 303, 983-988; Westover et al., (2004) *Science* 303, 1014-1016; Armache, et al., (2003) *Proc. Natl. Acad. Sci. USA* 100, 6964-6968). Moreover, cryo-EM structures have been determined for bacterial RNAP and eukaryotic RNAP I (Opalka, et al. (2000) *Proc. Natl. Acad. Sci. USA* 97, 617-622; Darst, et al. (2002) *Proc. Natl. Acad. Sci. USA* 99, 4296-4301; DeCarlo, et al. (2003) *J. Mol. Biol.* 329, 891-902).

Structures also have been determined for RNAP complexes with nucleic acids, nucleotides and inhibitors (Campbell, et al. (2001) *Cell* 104, 901-912; Artsimovitch, et al. (2005) *Cell* 122, 351-363; Campbell, et al. (2005) *EMBO J.* 24, 674-682; Artsimovitch, et al. (2004) *Cell* 117, 299-310; Tuske, et al. (2005) *Cell* 122, 541-522; Temiaov, et al. (2005) *Mol. Cell.* 19, 655-666; Vassulyev, et al. (2005) *Nature Structl. Biol.* 12, 1086-1093; Gnatt, et al. (2001) *Science* 292, 1876-1882; Westover, et al. (2004a) *Science* 303, 1014-1016; Westover, et al. (2004b) *Cell* 119, 481-489; Ketenberger, et al. (2004) *Mol. Cell.* 16, 955-965; Bushnell, et al. (2002) *Proc. Natl. Acad. Sci. U.S.A.* 99, 1218-1222; Kettenberger, et al. (2005) *Natl. Structl. Mol. Biol.* 13, 44-48).

The structures reveal that RNAP—bacterial or eukaryotic—has a shape reminiscent of a crab claw. The two "pincers" of the "claw" define the active-center cleft that can accommodate a double-stranded nucleic acid-and which has the active-center $Mg^{2+}$ at its base. The largest subunit (β' in bacterial RNAP) makes up one pincer, termed the "clamp," and part of the base of the active-center cleft. The second-largest subunit (β in bacterial RNAP) makes up the other pincer and part of the base of the active-center cleft.

Moreover, based on the structures, as well as biophysical and biochemical results, models have been proposed for the structures of transcription initiation and elongation complexes (Gnatt et al., (2001) Science 292, 1876-1882; Ebright, R. (2000) J. Mol. Biol. 304, 687-689; Naryshkin, et al., (2000) Cell 101, 601-611); Kim et al., (2000) Science 288, 1418-1421; Korzheva, et al., (2000) Science 289, 619-625; and Mekler et al., (2002) Cell 108:599-614). The models propose that nucleic acids completely fill the active-center cleft of RNAP, such that the only route by which incoming nucleoside triphosphate substrates (NTPs) can access the active center is through an approximately 25 Å long, 10 Å wide tunnel known as the "secondary channel" or "pore," that bores through the floor of the active-center cleft of RNAP opposite the active-center cleft.

Microcin J25 (MccJ25) (SEQ ID NO:1) is a 21-amino acid bactericidal peptide, which is produced by some strains of intestinal bacterium *E. coli*. MccJ25 inhibits the growth of Gram-negative bacteria by binding to RNA polymerase. MccJ25 is extremely stable and is potentially useful as an antibacterial and decontamination agent. However, Gram-negative bacteria can become resistant to MccJ25 due to mutations that interfere with MccJ25 uptake or due to mutations in RNA polymerase genes. Moreover, Gram-positive bacteria are resistant to MccJ25, since the drug does not bind to RNA polymerases from these organisms.

The RNA polymerase site interacting with MccJ25 was previously defined by mapping MccJ25-resistance mutations in RNAP (Yuzenkova, et al. (2002) J. Biol. Chem. 277, 50867-50875). The mutations mapped around the circumference of the RNAP secondary channel described above. These results suggested that MccJ25 blocks the channel. This suggestion was validated through biochemical, single-molecule, and kinetic analyses (Adelman, et al. (2004) Mol. Cell. 16, 753-762). Moreover, it was previously determined that mature MccJ25 assumes a highly unusual "threaded lasso" structure (Wilson, et al. (2003) J. Am. Chem. Soc. 125, 12475-12483).

It would be desirable to provide further peptide antibiotics capable of inhibiting bacterial cell growth by binding to RNA polymerase. In particular, it would be desirable to provide MccJ25 variants with desired specificity toward target bacteria.

SUMMARY OF THE INVENTION

Applicants have discovered analogs of MccJ25 that are able to bind to bacterial RNAP, to inhibit bacterial RNAP, and to inhibit bacterial growth with a potency at least equal to that of mature MccJ25 (FIG. 1).

The present invention provides an analog of bacteriocidal peptide microcin J25 (MccJ25) that (1) has an amino acid sequence that differs from that of MccJ25 by having at least one amino acid substitution; and (2) that inhibits bacterial cell growth with a potency at least equal to that of MccJ25.

The present invention also provides a method of identifying at least one MccJ25 analog that inhibits growth of MccJ25-sensitive cells. This method includes growing MccJ25-sensitive cells in the presence of cells harboring a plasmid containing an MccJ25 analog, the analog having an amino acid sequence that differs from that of MccJ25 by having at least one amino acid substitution; and observing the presence or absence of cell growth inhibition, wherein the presence of cell growth inhibition indicates the presence of cells producing the MccJ25 analog that inhibits growth of MccJ25-sensitive cells.

The invention further provides a method of identifying at least one MccJ25 analog that inhibits cell growth of MccJ25-resistant cells. This method includes growing MccJ25-resistant cells in the presence of cells harboring a plasmid containing an MccJ25 analog, the analog having an amino acid sequence that differs from that of MccJ25 by having at least one amino acid substitution. The method also includes observing the presence or absence of cell growth inhibition, wherein the presence of cell growth inhibition indicates the presence of cells producing the MccJ25 analog that inhibits growth of MccJ25-resistant cells.

It is anticipated that compounds and methods of this invention would have applications not only in antibacterial therapy, but also in: (a) identification of bacterial RNAP (diagnostics, environmental-monitoring, and sensors applications), (b) labeling of bacterial RNAP (diagnostics, environmental-monitoring, imaging, and sensors applications), (c) immobilization of bacterial RNAP (diagnostics, environmental-monitoring, and sensors applications), (d) purification of bacterial RNA polymerase (biotechnology applications), (e) regulation of bacterial gene expression (biotechnology applications), and (f) antisepsis (antiseptics, disinfectants, and advanced-materials applications).

These and other aspects of the present invention will be better appreciated by reference to the following drawings and Detailed Description The file of this patent contains at least one drawing executed in color. Copies of this patent with color drawing(s) will be provided by the Patent and Trademark Office upon request and payment of the necessary fee.

BRIEF DESCRIPTION OF THE DRAWINGS

As shown in FIG. 1, each of the following MccJ25 analogs was found to have an activity level greater than or equal to wild-type MccJ25 (SEQ ID NO:1): [$Ser_3$] MccJ25 (SEQ ID NO:2), [$Ile_6$] MccJ25 (SEQ ID NO:3), [$Phe_6$] MccJ25 (SEQ ID NO:4), [$Ala_{11}$] MccJ25 (SEQ ID NO:5), [$Trp_{11}$] MccJ25 (SEQ ID NO:6), [$Thr_{12}$] MccJ25 (SEQ ID NO:7), [$Ser_{12}$] MccJ25 (SEQ ID NO:8), [$Met_{12}$] MccJ25 (SEQ ID NO:9), [$His_{12}$] MccJ25 (SEQ ID NO:10), [$Leu_{13}$] MccJ25 (SEQ ID NO:11), [$Ala_{13}$] MccJ25 (SEQ ID NO:12), [$Asn_{13}$] MccJ25 (SEQ ID NO:13), [$Arg_{13}$] MccJ25 (SEQ ID NO:14), [$Pro_{13}$] MccJ25 (SEQ ID NO:15), [$Thr_{13}$] MccJ25 (SEQ ID NO:16), [$His_{13}$] MccJ25 (SEQ ID NO:17), [$Val_{13}$] MccJ25 (SEQ ID NO:18), [$Met_{13}$] MccJ25 (SEQ ID NO:19), [$Phe_{13}$] MccJ25 (SEQ ID NO:20), [$Trp_{13}$] MccJ25 (SEQ ID NO:21), [$Ser_{14}$] MccJ25 (SEQ ID NO:22), [$Thr_{14}$] MccJ25 (SEQ ID NO:23), [$Phe_{15}$] MccJ25 (SEQ ID NO:24), [$Gly_{15}$] MccJ25 (SEQ ID NO:25), [$Leu_{15}$] MccJ25 (SEQ ID NO:26), [$His_{15}$] MccJ25 (SEQ ID NO:27), [$Asn_{15}$] MccJ25 (SEQ ID NO:28), [$Ala_{15}$] MccJ25 (SEQ ID NO:29), [$Ile_{15}$] MccJ25 (SEQ ID NO:30), [$Trp_{15}$] MccJ25 (SEQ ID NO:31), [$Met_{15}$] MccJ25 (SEQ ID NO:32), [$Gln_{16}$] MccJ25 (SEQ ID NO:33), [$Glu_{17}$] MccJ25 (SEQ ID NO:34), [$Val_{17}$] MccJ25 (SEQ ID NO:35) and combinations thereof.

FIG. 4 illustrates the location of MccJ25-resistant mutations in RNA polymerase (red and purple) and structural modeling of MccJ25 (green) interaction with RNA polymerase.

FIG. 5 illustrates one embodiment of a biological test for mutant mcjA activity.

FIG. 9 illustrates representative mass-spectra of wild-type MccJ25 (SEQ ID NO:1) and MccJ25 mutants. The mutants shown are Y20F (SEQ ID NO:37) and Y20G (SEQ ID NO:38), which are inactive, and I13A (SEQ ID NO:12), which is active.

FIG. 10 illustrates the comparison of in vitro transcription results obtained with wild-type MccJ25 (SEQ ID NO:1) and a MccJ25 mutant (MccJ25$^{TL}$; SEQ ID NO:39), which is inactive in vivo.

DETAILED DESCRIPTION

The present invention provides specific inhibitors of bacterial RNAP, the enzyme responsible for transcription. The invention has applications in control of bacterial gene expression, control of bacterial growth, antibacterial chemistry, and antibacterial therapy.

As described above, Microcin J25 (MccJ25; SEQ ID NO:1), is a 21-amino acid bacterial peptide produced by some strains of intestinal bacterium E. Coli. It is known that MccJ25 inhibits the growth of Gram-negative bacteria by binding to RNA polymerase. MccJ25 is extremely stable and is potentially useful as an antibacterial and decontamination agent. However, Gram-negative bacteria can become resistant to MccJ25 due to mutations that interfere with MccJ25 uptake or due to mutations in RNA polymerase genes. Gram-positive bacteria, which include such important pathogens as S. aureus and B. anthracis are resistant to wild-type MccJ25, since the drug does not bind to RNA polymerases from these organisms.

Figure 2:
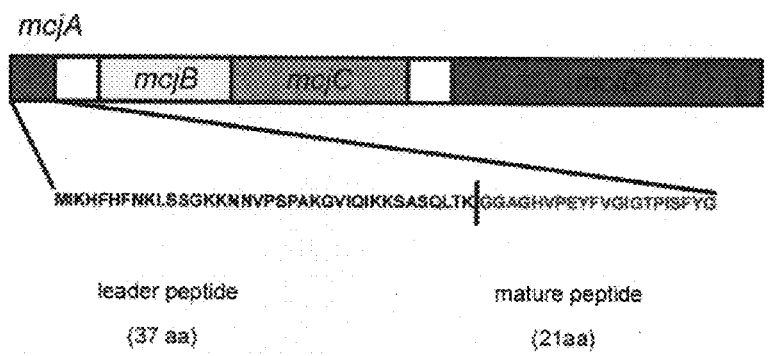
FIG. 2 illustrates a plasmid-borne mcj gene cluster encoding MccJ25. The 58 amino acid long MccJ25 precursor McjA (SEQ ID NO:36) is shown.

As shown in FIG. 2, MccJ25 is encoded by a plasmid-born mcj gene cluster. The 58 amino acid long MccJ25 precursor mcjA (SEQ ID NO:36) is processed by products of the mcjB and mcjC genes to yield mature MccJ25. The product of the mcjD gene is a MccJ25 exporter.

Figure 3:
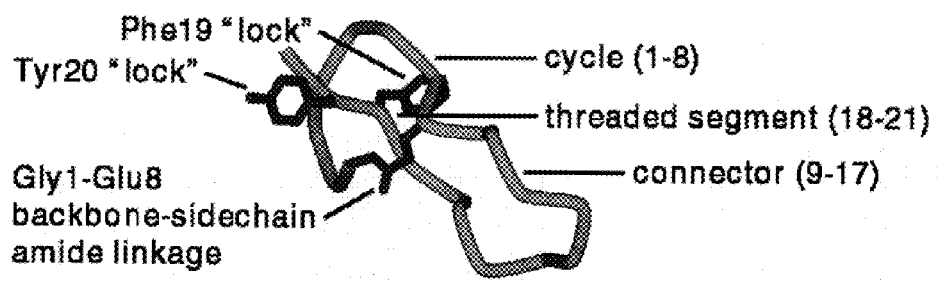
FIG. 3 illustrates the "threaded lasso" structure of mature MccJ25.

As shown in FIG. 3, mature MccJ25 assumes a highly unusual "threaded lasso" fold. As a result of the threaded lasso structure, MccJ25 is extremely stable.

Since MccJ25 is ribosomally synthesized, Applicants employed molecular genetic approaches in order to generate multiple MccJ25 variants followed by direct selection of MccJ25 derivatives with desired specificity towards target bacteria. In order to increase the spectrum of MccJ25 antibacterial action and its usefulness, Applicants initiated systematic mutational analysis of the MccJ25 portion of the mcjA gene coding for MccJ25 precursor. The goal was to obtain all 399 (21 MccJ25 amino acid positions×19 non-wild-type amino acids per position) single substitutions of MccJ25 and to characterize their ability to assemble into the mature threaded lasso structure, to inhibit cell growth, and to inhibit transcription. Examples of these substitution mutants include, but are not limited to, those shown in FIG. 1.

In order to characterize the activity of the substitution mutants, Applicants performed biological tests for mutant mcj activity. In particular, as described in the examples section, Applicants assessed the ability of the mutants to inhibit cell growth of MccJ25-sensitive cells. For example, cells harboring a plasmid containing a MccJ25 mutant were spotted on the surface of a bottom agar layer and allowed to grow overnight. Thereafter, a lawn of MccJ25-sensitive cells in soft agar was poured on top of the bottom agar layer, and cell growth inhibition zones in the top agar layer were observed. Applicants found that cells producing some MccJ25 mutants produced growth inhibition zones that were larger than those produced by control wild-type MccJ24-producing cells. Other MccJ25 mutants produced inhibition zones that were equal to or smaller than the wild-type MccJ25-producing cells. Moreover, cells containing some other mutant mcjA plasmids produced no inhibition zones. The lack of cell growth inhibition could be due to the absence of mature MccJ25 production, failure of muant MccJ25 to enter *E. Coli*, or to inhibit RNAP.

In order to differentiate between these possibilities, Applicants performed micropurification of mutant MccJ25 followed by mass spectral analysis (MALDI-MS) in order to assess (1) mature MccJ25 production and (2) whether the MccJ25 mutant matures into a threaded lasso structure characteristic of mature MccJ25.

Figure 1:
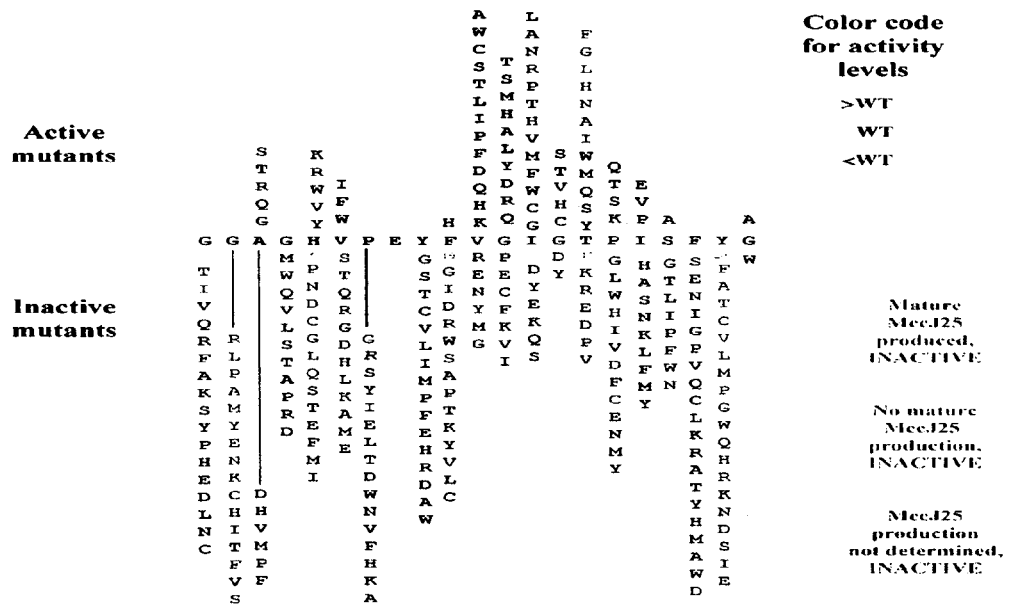
FIG. 1 illustrates MccJ25 mutants, which are shown above and below the MccJ25 wild-type sequence. Mutants above the MccJ25 sequences are color-coded according to their activity. Mutants below the MccJ25 sequence are inactive.

The results of the analyses of mutants available so far are summarized in FIG. 1. With reference to FIG. 1, MccJ25 mutants are shown above and below the MccJ25 sequence (SEQ ID NO:1) (single-letter amino acid code). Mutants above the MccJ25 sequence are color-coded according to their activity. Mutants below the MccJ25 sequence are inactive. Active mutants color-coded in red had an activity level greater than wild-type MccJ25; active mutants color-coded in black had an activity level about equal to that of wild-type MccJ25.

Accordingly, the present invention provides an analog of bacteriocidal peptide microcin J25 (MccJ25) that (1) has an amino acid sequence that differs from that of MccJ25 by having at least one amino acid substitution; and (2) that inhibits bacterial cell growth with a potency at least equal to that of MccJ25. The terms "analog" and "mutant" may be used interchangeably throughout the specification.

In some embodiments, the MccJ25 analog is selected from the following: $[Ser_3]$ MccJ25 (SEQ ID NO:2), $[Ile_6]$ MccJ25 (SEQ ID NO:3), $[Phe_6]$ MccJ25 (SEQ ID NO:4), $[Ala_{11}]$ MccJ25 (SEQ ID NO:5), $[Trp_{11}]$ MccJ25 (SEQ ID NO:6), $[Thr_{12}]$ MccJ25 (SEQ ID NO:7), $[Ser_{12}]$ MccJ25 (SEQ ID NO:8), $[Met_{12}]$ MccJ25 (SEQ ID NO:9), $[His_{12}]$ MccJ25 (SEQ ID NO:10), $[Leu_{13}]$ MccJ25 (SEQ ID NO:11), $[Ala_{13}]$ MccJ25 (SEQ ID NO:12), $[Asn_{13}]$ MccJ25 (SEQ ID NO:13), $[Arg_{13}]$ MccJ25 (SEQ ID NO:14), $[Pro_{13}]$ MccJ25 (SEQ ID NO:15), $[Thr_{13}]$ MccJ25 (SEQ ID NO:16), $[His_{13}]$ MccJ25 (SEQ ID NO:17), $[Val_{13}]$ MccJ25 (SEQ ID NO:18), $[Met_{13}]$ MccJ25 (SEQ ID NO:19), $[Phe_{13}]$ MccJ25 (SEQ ID NO:20), $[Trp_{13}]$ MccJ25 (SEQ ID NO:21), $[Ser_{14}]$ MccJ25 (SEQ ID NO:22), $[Thr_{14}]$ MccJ25 (SEQ ID NO:23), $[Phe_{15}]$ MccJ25 (SEQ ID NO:24), $[Gly_{15}]$ MccJ25 (SEQ ID NO:25), $[Leu_{15}]$ MccJ25 (SEQ ID NO:26), $[His_{15}]$ MccJ25 (SEQ ID NO:27), $[Asn_{15}]$ MccJ25 (SEQ ID NO:28), $[Ala_{15}]$ MccJ25 (SEQ ID NO:29), $[Ile_{15}]$ MccJ25 (SEQ ID NO:30), $[Trp_{15}]$ MccJ25 (SEQ ID NO:31), $[Met_{15}]$ MccJ25 (SEQ ID NO:32), $[Gln_{16}]$ MccJ25 (SEQ ID NO:33), $[Glu_{17}]$ MccJ25 (SEQ ID NO:34), $[Val_{17}]$ MccJ25 (SEQ ID NO:35) and combinations thereof. As shown in FIG. 1, each of these analogs was found to have an activity level greater than or equal to wild-type MccJ25.

In some other embodiments, the analog is selected from the following: $[Leu_{13}]$ MccJ25 (SEQ ID NO:11), $[Ala_{13}]$ MccJ25 (SEQ ID NO:12), $[Asn_{13}]$ MccJ25 (SEQ ID NO:13), $[Arg_{13}]$ MccJ25 (SEQ ID NO:14), $[Pro_{13}]$ MccJ25 (SEQ ID NO:15), $[Thr_{13}]$ MccJ25 (SEQ ID NO:16) and $[His_{13}]$ MccJ25 (SEQ ID NO:17). As shown in FIG. 1, each of these analogs was found to have an activity level greater than wild-type MccJ25.

In some further embodiments, the analog is selected from the following: $[Phe_{15}]$ MccJ25 (SEQ ID NO:24), $[Gly_{15}]$ MccJ25 (SEQ ID NO:25), $[Leu_{15}]$ MccJ25 (SEQ ID NO:26), $[His_{15}]$ MccJ25 (SEQ ID NO:27), $[Asn_{15}]$ MccJ25 (SEQ ID NO:28), $[Ala_{15}]$ MccJ25 (SEQ ID NO:29) and $[Ile_{15}]$ MccJ25 (SEQ ID NO:30). As shown in FIG. 1, each of these analogs was found to have an activity level greater than wild-type MccJ25.

An analog according to the present invention may include a detectable group. In some embodiments, the detectable group is selected from chromophores, fluorophores, and cyanine dyes. The detectable group may be located at the site of the amino acid substitution.

As described above, the RNA polymerase site interacting with MccJ25 was previously defined by mapping MccJ25-resistant mutations in RNA polymerase (Yuzenkova, et al. (2002) J. Biol. Chem. 277, 50867-50875). With reference to FIG. 4, the location of the substitutions leading to MccJ25 resistance (red and purple) and structural modeling of MccJ25 (green) interaction with RNAP suggests that the mechanism of transcription inhibition by MccJ25 consists of occlusion of the RNAP secondary channel and prevention of substrate traffic to the enzyme's catalytic center (white sphere on the left panel). This suggestion was validated, for example, by experiments disclosed in copending, commonly owned U.S. application Ser. No. 10/526,323, filed Feb. 28, 2005, the entire contents of which are incorporated herein by reference. In particular, U.S. application Ser. No. 10/526,323 discloses that blocking the RNAP secondary channel with MccJ25 prevents uptake of NTPs by RNAP and thus inhibits transcription. Active MccJ25 mutants provided herein may similarly be predicted to occlude the RNAP secondary channel and block access of substrates (e.g., NTPs) to the active center of RNAP.

As described above, MccJ25 binds within the RNAP secondary channel. For example, as disclosed in U.S. application Ser. No. 10/526,323, filed Feb. 28, 2005, the RNAP secondary channel contains a multi-residue determinant for function of MccJ25. Obstruction of the RNAP secondary channel represents a novel mechanism of inhibition of RNAP. Obstruction of the RNAP secondary channel represents an exceptionally attractive target for development of novel antibacterial agents, including, but not limited to, those described herein, as well as in copending, commonly-owned U.S. application Ser. No. 10/526,323, filed Feb. 28, 2005. First, the RNAP secondary channel is eminently "druggable," presenting an extended, encircling surface complementary to a range of molecules—like MccJ25 and the MccJ25 analogs provided herein—that have molecular weights of 500-2,500 Da. Second, the RNAP secondary channel exhibits distinct patterns of sequence conservation in bacterial RNAP and eukaryotic RNAP, permitting identification of MccJ25 analogs that inhibit bacterial RNAP but do not inhibit eukaryotic RNAP. Third, the RNAP secondary channel is distinct from, and well-separated from, the binding site of the RNAP inhibitor in current use in antimicrobial therapy, rifampicin—permitting identification of MccJ25 analogs that do not exhibit cross-resistance with rifampicin.

The invention provides analogs of MccJ25 that bind to RNAP from a bacterial species. The invention also provides analogs of MccJ25 that inhibit an activity of RNAP from a bacterial species. The invention also provides analogs of MccJ25 that inhibit at least one of viability of a bacterium and growth of a bacterium.

The invention also provides for use of an analog of MccJ25 having an activity level about equal to or greater than wild-type MccJ25 to control bacterial gene expression.

The invention also provides for use of an analog of MccJ25 having an activity level about equal to or greater than wild-type MccJ25 to control bacterial viability or bacterial growth.

The invention also provides for use of an analog of MccJ25 having an activity level about equal to or greater than wild-type MccJ25 as an antibacterial agent.

One preferred aspect of the invention provides for an analog of MccJ25 having an activity level about equal to or greater than wild-type MccJ25 that binds to RNAP from a bacterial species, but does not bind, or binds less well, to RNAP from a mammalian species.

Another preferred aspect of the invention provides for an analog of MccJ25 having an activity level about equal to or greater than wild-type MccJ25 that inhibits biochemical activity of RNAP (e.g., uptake of NTPs mediated by the secondary channel) from a bacterial species, but does not inhibit biochemical activity, or inhibits biochemical activity less well, of RNAP from a mammalian species.

Another preferred aspect of the invention provides for an analog of MccJ25 having an activity level about equal to or greater than wild-type MccJ25 that inhibits viability or growth of a bacterial species, but does not inhibit viability or growth, or inhibits viability or growth less well, of a mammalian species.

Another preferred aspect of the invention provides for an analog of MccJ25 having an activity level about equal to or greater than wild-type MccJ25 that binds to and/or inhibits RNAP from a broad spectrum of bacterial species.

Another preferred aspect of the invention provides for an analog of MccJ25 having an activity level about equal to or greater than wild-type MccJ25 that binds to and/or inhibits RNAP from a broad spectrum of Gram-negative bacterial species. In some embodiments, the MccJ25 analog may bind to and/or inhibit RNAPs harboring secondary channel mutations that lead to resistance to wild-type MccJ25.

Another preferred aspect of the invention provides for an analog of MccJ25 that binds to and/or inhibits RNAP from a broad spectrum of Gram-positive bacterial species. As described above, wild-type MccJ25 does not bind to RNAP from Gram-positive bacteria. However, it is well within the contemplation of the present invention that one or more of the MccJ25 analogs herein provided may be useful in this regard.

Another preferred aspect of the invention provides for an analog of MccJ25 that binds to and/or inhibits RNAP from a broad spectrum of both Gram-negative and Gram-positive bacterial species.

The present invention further relates to a method for identifying MccJ25 analogs that inhibit viability and/or growth of a bacterium. In some embodiments, the MccJ25 analog binds to a region within the RNAP secondary channel. In some embodiments, the MccJ25 analog is selected from the following: [Ser$_3$]MccJ25 (SEQ ID NO:2), [Ile$_6$]MccJ25 (SEQ ID NO:3), [Phe$_6$]MccJ25 (SEQ ID NO:4), [Ala$_{11}$]MccJ25 (SEQ ID NO:5), [Trp$_{11}$] MccJ25 (SEQ ID NO:6), [Thr$_{12}$] MccJ25 (SEQ ID NO:7), [Ser$_{12}$] MccJ25 (SEQ ID NO:8), [Met$_{12}$] MccJ25 (SEQ ID NO:9), [His$_{12}$] MccJ25 (SEQ ID NO:10), [Leu$_{13}$] MccJ25 (SEQ ID NO:11), [Ala$_{13}$] MccJ25 (SEQ ID NO:12), [Asn$_{13}$] MccJ25 (SEQ ID NO:13), [Arg$_{13}$] MccJ25 (SEQ ID NO:14), [Pro$_{13}$] MccJ25 (SEQ ID NO:15), [Thr$_{13}$] MccJ25 (SEQ ID NO:16), [His$_{13}$] MccJ25 (SEQ ID NO:17), [Val$_{13}$] MccJ25 (SEQ ID NO:18), [Met$_{13}$] MccJ25 (SEQ ID NO:19), [Phe$_{13}$] MccJ25 (SEQ ID NO:20) [Trp$_{13}$] MccJ25 (SEQ ID NO:21), [Ser$_{14}$] MccJ25 (SEQ ID NO:22), [Thr$_{14}$] MccJ25 (SEQ ID NO:23), [Phe$_{15}$] MccJ25 (SEQ ID NO:24), [Gly$_{15}$] MccJ25 (SEQ ID NO:25), [Leu$_{15}$] MccJ25 (SEQ ID NO:26), [His$_{15}$] MccJ25 (SEQ ID NO:27), [Asn$_{15}$] MccJ25 (SEQ ID NO:28), [Ala$_{15}$] MccJ25 (SEQ ID NO:29), [Ile$_{15}$] MccJ25 (SEQ ID NO:30), [Trp$_{15}$] MccJ25 (SEQ ID NO:31), [Met$_{15}$] MccJ25 (SEQ ID NO:32), [Gln$_{16}$] MccJ25 (SEQ ID NO:33), [Glu$_{17}$] MccJ25 (SEQ ID NO:34), [Val$_{17}$] MccJ25 (SEQ ID NO:35) and combinations thereof. Each of these analogs was found to inhibit viability and/or growth of a bacterium and had an activity level about equal to or greater than wild-type MccJ25.

Isolation of RNAP:

The bacterial RNAP, or bacterial RNAP derivative, can be isolated from bacteria, produced by recombinant methods, or produced through in vitro protein synthesis. Various compounds can be introduced to determine whether a tested compound (e.g., an analog of MccJ25) binds to, inhibits an activity of, or displaces a detectable-group-containing molecule from, the bacterial RNAP or RNAP derivative in a secondary-channel-target-dependent manner.

Assays can be performed in vitro or in vivo, and do not necessarily require isolation of bacterial RNAP or bacterial RNAP derivative.

Test compounds can include peptides. Test compounds alternatively, or in addition, can include non-peptide chemical compounds.

Assay Components:

The bacterial RNAP, or RNAP fragment or derivative, containing the secondary channel, and an inhibitory compound specific to the secondary channel of RNAP (e.g., MccJ25 or an analog thereof), which are binding partners used as components in the assay, may be derived from natural sources (e.g., purified from bacterial RNAP using protein separation techniques well known in the art); produced by recombinant DNA technology using techniques known in the art (see, e.g., Sambrook et al., 1989, Molecular Cloning: A Laboratory Manual, Cold Spring Harbor Laboratories Press, Cold Spring Harbor, N.Y.); and/or chemically synthesized in whole or in part using techniques known in the art (see, e.g., Creighton, 1983, Proteins: Structures and Molecular Principles, W.H. Freeman & Co., N.Y., pp. 50-60).

Where recombinant DNA technology is used to produce the bacterial RNAP, RNAP fragment, or derivative containing the secondary channel and MccJ25 (or MccJ25 analog) binding partner, it may be advantageous to engineer fusion proteins that can facilitate labeling, immobilization and/or detection. For example, the coding sequence of a bacterial RNAP secondary channel can be fused to that of a heterologous protein that has enzyme activity or serves as an enzyme substrate in order to facilitate labeling and detection. The fusion constructs should be designed so that the heterologous component of the fusion product does not interfere with binding of the bacterial RNAP secondary channel region and an inhibitory compound specific to the secondary channel region of RNAP (e.g., MccJ25 or an analog thereof).

For a binding assay, one of the binding partners used in the assay system may be labeled, either directly or indirectly, to facilitate detection of a complex formed between the bacterial RNAP secondary channel region and an inhibitory compound specific to the secondary channel of RNAP. Any of a variety of suitable labeling systems may be used including, but not limited to, radioisotopes such as $^{125}$I; enzyme labeling systems that generate a detectable calorimetric signal or light when exposed to substrate; and fluorescent labels.

Fluorescent Labels are Preferred.

Indirect labeling involves the use of a third protein, such as a labeled antibody, which specifically binds to an entity containing a secondary channel-region target. Such antibodies include, but are not limited to, polyclonal, monoclonal, chimeric, humanized, single chain, Fab fragments and fragments produced by an Fab expression library.

For the production of antibodies, various host animals may be immunized by injection with at least one segment of an entity containing a secondary channel-region target. Such host animals may include, but are not limited to, rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies may be prepared by using any technique that provides for the production of antibody molecules by continuous cell lines in culture. These include, but are not limited to, the hybridoma technique originally described by Kohler and Milstein, (1975) *Nature* 256:495-497), the human B-cell hybridoma technique (Kosbor et al. (1983) *Immunology Today*, 4:72, Cote et al. (1983) *Proc. Natl. Acad. Sci.,* 80:2026-2030) and the EBV-hybridoma technique (Cole et al., 1985, Monoclonal Antibodies and Cancer Therapy, Alan R. Liss, Inc., pp. 77-96). In addition, techniques developed for the production of "chimeric antibodies" (Morrison et al. (1984) *Proc. Natl. Acad. Sci.,* 81:6851-6855; Neuberger et al. (1984) *Nature,* 312:604-608; Takeda et al. (1985) *Nature,* 314:452-454) by splicing the genes from a mouse antibody molecule of appropriate antigen specificity together with genes from a human antibody molecule of appropriate biological activity. Alternatively, techniques described for the production of single-chain antibodies (e.g., U.S. Pat. No. 4,946,778) can be adapted to produce single-chain antibodies specific to the bacterial RNAP secondary channel.

Antibody fragments that recognize specific epitopes may be generated by known techniques. For example, such fragments include, but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al. (1989) *Science,* 246:1275-1281) to allow rapid and easy identification of monoclonal Fab fragments with the desired specificity.

Binding Assays:

Binding assays can be conducted in a heterogeneous or homogeneous format. A heterogeneous assay is an assay in which reaction results are monitored by separating and detecting at least one component during or following reaction. A homogeneous assay is an assay in which reaction results are monitored without separation of components.

In either approach, the order of addition of reactants can be varied to obtain different information about the compounds being tested.

In one example of a heterogeneous binding assay system, one binding partner—e.g., either an entity containing a RNAP secondary channel or a compound specific to the RNAP secondary channel (e.g., McCJ25 or an analog thereof)—is anchored onto a solid surface, and the other binding partner, which is not anchored, is labeled, either directly or indirectly. In practice, microtiter plates are conveniently utilized. The anchored species may be immobilized by non-covalent or covalent attachments. Alternatively, an immobilized antibody specific for the bacterial RNAP secondary channel may be used to anchor the bacterial RNAP secondary channel to the solid surface. The surfaces may be prepared in advance and stored. In order to conduct the assay, the non-immobilized binding partner is added to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the binding partner was pre-labeled, the detection of label immobilized on the surface indicates that complexes were formed. Where the binding partner is not pre-labeled, an indirect label can be used to detect complexes anchored on the surface; e.g., using a labeled antibody specific for the binding partner (the antibody, in turn, may be directly labeled or indirectly labeled with a labeled anti-Ig antibody). Depending upon the order of addition of reaction components, test compounds which inhibit complex formation or which disrupt preformed complexes can be detected.

In a preferred embodiment of the invention, a homogeneous binding assay is used. In one preferred embodiment of the invention, involving use of a homogeneous binding assay, a preformed complex of the bacterial RNAP secondary channel and a compound that binds to the RNAP secondary channel is prepared (e.g., McCJ25 or an analog thereof), in which at least one of the binding partners contains a detectable group having that exhibits a difference in a detectable property in the complex state and in the free state (see, e.g., U.S. Pat. No. 4,109,496); the addition of a test compound that competes with, and displaces, one of the binding partners from the preformed complex results in a change in a detectable properties of the detectable group, permitting identification of test substances able to bind to the secondary channel-region target.

One aspect of the invention provides fluorescence resonance energy transfer (FRET)-based homogeneous assays (Förster (1948) Ann. Physik. (Leipzig) 2, 55-75; reviewed in Lilley and Wilson (2000) Curr. Opin. Chem. Biol. 4, 507-517; Selvin, P (2000) *Nature Structl. Biol.* 7, 730-734; Mukhopadhyay et al., 2001 *Cell* 106, 453-463; Mekler, et al. (2002) *Cell* 108, 599-614; Mukhopadhyay, et al. (2004) *Mol. Cell.* 14, 739-751). FRET occurs in a system having a first fluorescent probe serving as a donor and a second fluorescent probe or chhomophore serving as an acceptor, where the emission wavelength of the donor overlaps the excitation wavelength of the acceptor. In such a system, upon excitation of the donor with light of its excitation wavelength, energy can be transferred from the donor to the acceptor, resulting in excitation of the acceptor and omission at the acceptor's emission wavelength. With commonly used fluorescent probes, FRET permits accurate determination of distances in the range of ~20 to ~100 Å. FRET permits accurate determination of distances up to more than one-half the diameter of a transcription complex (diameter ~150 Å; see Zhang et al. 1999; Cramer et al. (2001) *Science* 292, 1863-1876; Gnatt et al. (2001) *Science* 292, 1876-1882).

A preferred assay involves monitoring of FRET between: a) one of a fluorescent probe or a chromophore present in a bacterial RNAP, and b) one of a fluorescent probe or a chromophore present in a small molecule that binds to the RNAP secondary channel (e.g., McCJ25 or an analog thereof).

An especially preferred assay involves monitoring of FRET between: a) one of a fluorescent probe or a chromophore present in a bacterial RNAP, and b) one of a fluorescent probe or a chromophore present in an McCJ25 analog according to the present invention.

Activity Assays:

In a particular embodiment, the effect of a test compound on an activity of a bacterial RNAP, or a fragment thereof, is determined (either independently of, or subsequent to, a binding assay as exemplified above). In one such embodiment, the extent or rate of the DNA-dependent RNA synthesis is determined. For such assays, a labeled nucleotide can be used. The assay can include the withdrawal of aliquots from the incubation mixture at defined intervals and subsequent analysis.

Alternatively, the assay can be performed using a real-time assay (e.g., with a fluorescently labeled nucleotide or with a fluorescent probe for RNA).

One assay for RNAP activity is a modification of the method of Burgess et al. (*J. Biol. Chem.*, 244:6160 (1969); see http://www.worthington-biochem.com/manual/R/RNAP.html). One unit incorporates one nanomole of UMP into acid insoluble products in 10 minutes at 37° C. under the assay conditions such as those listed below. The suggested assay conditions are: (a) 0.04 M Tris-HCl, pH 7.9, containing 0.01 M $MgCl_2$, 0.15 M KCl, and 0.5 mg/ml BSA; (b) nucleoside triphosphates (NTP): 0.15 mM each of ATP, CTP, GTP, UTP; spiked with $^3$H-UTP 75000-150000 cpms/0.1 ml; (c) 0.15 mg/ml calf thymus DNA; (d) 10% cold perchloric acid; and (e) 1% cold perchloric acid. A starting enzyme concentration of 0.1-0.5 units of RNAP in 5 μl-10 μl are used as the starting enzyme concentration.

The procedure is to add 0.1 ml Tris-HCl, 0.1 ml NTP and 0.1 ml DNA to a test tube for each sample or blank. At time zero, enzyme (or buffer for blank) is added to each test tube, and the contents are then mixed and incubated at 37° C. for 10 minutes. 1 ml of 10% perchloric acid is added to the tubes to stop the reaction. The acid insoluble products can be collected by vacuum filtration through Millipore filter discs having a pore size of 0.45 u-10 u (or equivalent). The filters are then washed four times with 1% cold perchloric acid using 1 ml-3 ml for each wash. These filters are then placed in scintillation vials. Two ml of methyl cellosolve are added to the scintillation vials to dissolve the filters. When the filters are completely dissolved (after about five minutes) 10 ml of scintillation fluid are added and the vials are counted in a scintillation counter.

Additional assays for analysis of RNAP activity contemplated by the present invention include fluorescence-detected abortive initiation assays, fluorescence-detected transcription assays, and molecular-beacon-based transcription assays. An especially preferred assay is the fluorescence-detected abortive initiation assay (see Example 4).

In assays of RNAP activity, different orders of addition of components may be employed. In preferred embodiments, an order of addition is employed in which RNAP or RNAP derivative is pre-incubated with the test compound—affording time and opportunity for formation of a complex between RNAP or RNAP derivative and the test compound—before RNAP is incubated with DNA.

Antibacterial Assays:

Methods of testing a compound for antibacterial activity in cultures are well known in the art, and can include standard assays of minimum inhibitory concentration (MIC; and of minimum bacteriocidal concentration (MBC). An especially preferred assay is the biological test described in Example 2.

With reference to FIG. 5 and Example 2, a method of testing an MccJ25 analog for antibacterial activity can include spotting cells harboring a plasmid containing an MccJ25 mutant on the surface of a bottom agar layer in a petri dish and allowing these cells to grow overnight. Thereafter, a lawn of MccJ25-sensitive cells in soft agar may be poured on top of the bottom agar layer, and cell growth inhibition zones in the solidified top agar layer may be observed.

Animal Model Assays:

Inhibitors of bacterial RNAP identified by the processes of the present invention can be assayed in animal experiments. The ability of an inhibitor to control bacterial infection can be assayed in animal models that are natural hosts for the bacterial species of interest. Such animal models may involve mammals, such as rodents, dogs, pigs, horses, and primates. Such animal models can be used to determine the $LD_{50}$ and the $ED_{50}$ in animal subjects, and such data can be used to derive the therapeutic index for the inhibitor. In animal models, test compounds can be administered by a variety of routes including topical, oral, subcutaneous, and intraperitoneal routes, depending on the proposed use. Generally, at least two groups of animals are used in the assay, with at least one group being a control group, which is administered the administration vehicle without the test compound.

Pharmaceutical Preparations and Methods of Administration:

Identified compounds that inhibit bacterial replication can be administered to a patient at therapeutically effective doses to treat bacterial infection. A therapeutically effective dose refers to that amount of the compound sufficient to result in amelioration of symptoms of bacterial infection.

Toxicity and therapeutic efficacy of such compounds can be determined by standard pharmaceutical procedures in cell cultures or experimental animals for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of infection in order to minimize damage to uninfected cells and reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal infection, or a half-maximal inhibition) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

EXAMPLES

Example 1

Generation of mcJA Mutants and High-Throughput Screening

Systematic mutational analysis of the MccJ25 portion of the mcjA gene coding for the MccJ25 precursor was initiated. The goal was to obtain all 399 (21 MccJ25 amino acid positions×19 non-wild-type amino acids per position) single substitutions of MccJ25 and to characterize their ability to assemble into the mature threaded lasso structure (FIG. 3), to inhibit cell growth, and to inhibit transcription. Degenerate DNA oligonucleotides were used to randomize each of the 21 MccJ25 codons of mcjA cloned on a plasmid that also contained genes coding for MccJ25 maturation enzymes (mcjBC) and the immunity pump (mcjD). In order to obtain the MccJ25 mutants (analogs) herein described, Stratagene's QuikChange Site-Directed Mutagenesis kit was used. Stratagene's QuikChange Site Directed Mutagenesis Kit is a simplified method to perform point mutations, change amino acids or delete/insert amino acids using a thermal cycling technique in combination with Dpn I digestion.

The procedure began with the mcjA gene of interest in a double strand vector, purified using a plasmid-prep kit (For example, from Qiagen). Two primers, both containing the desired mutation, covered the area where the mutation was to be made. A detailed set of instructions were contained in the manufacturer's protocol for primer design and were followed. In general, the desired mutation was kept towards the middle of the primer and the primers were purified by FPLC or PAGE when ordering.

Figure 6:
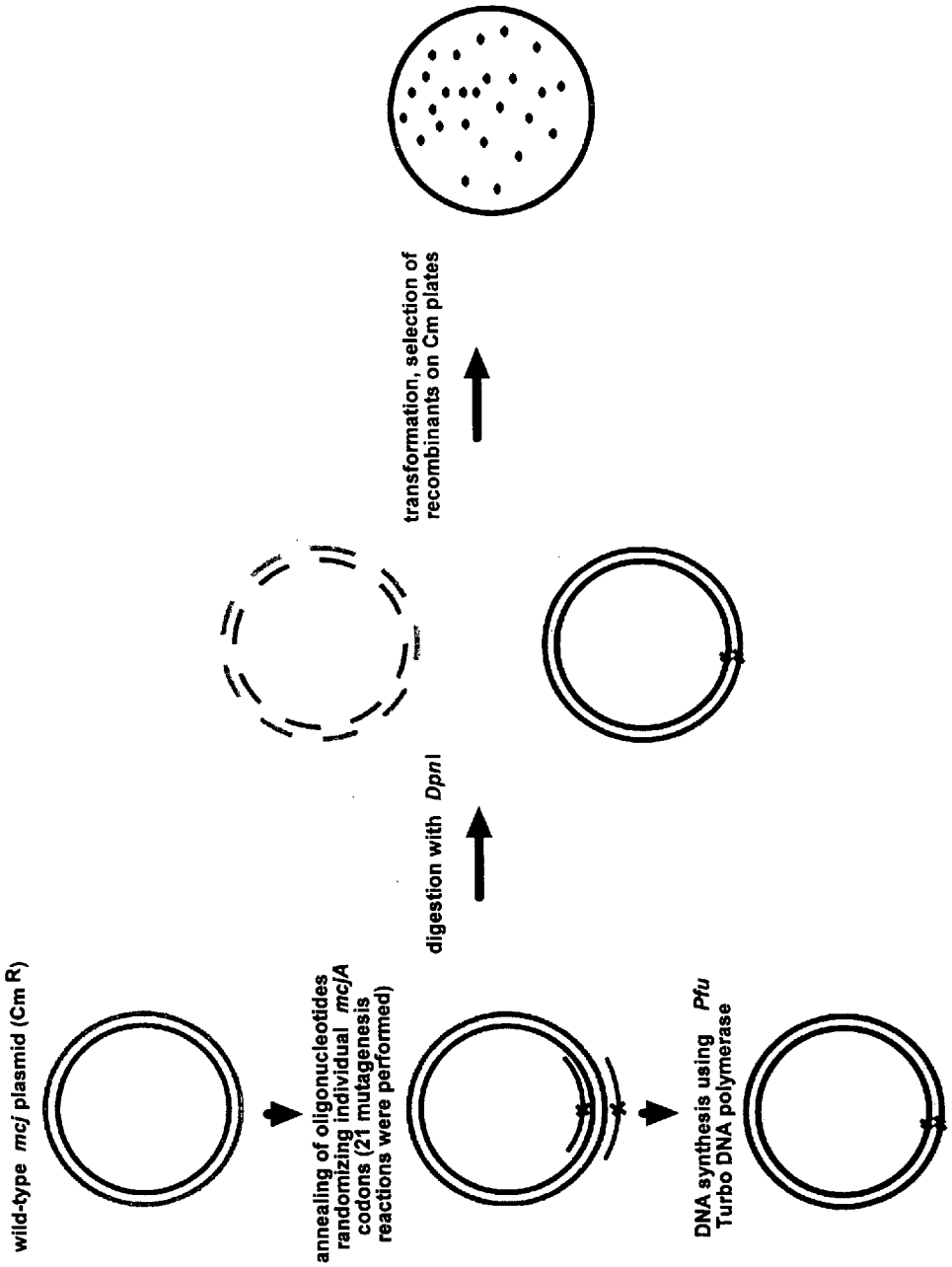
FIG. 6 illustrates the procedure used for generation of mcjA mutants.
Figure 7:
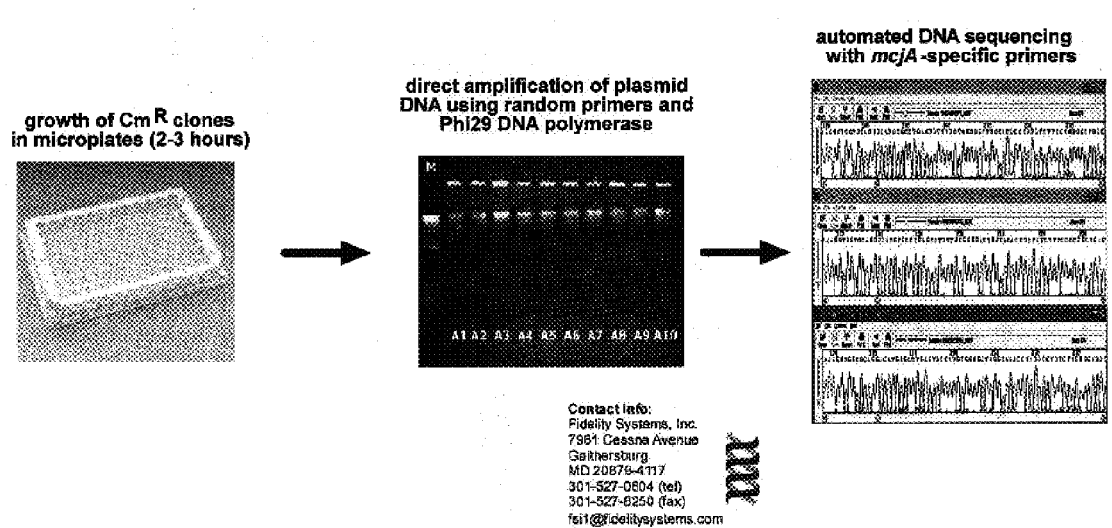
FIG. 7 illustrates high-throughput DNA-sequencing of the recombinants generated using the procedure in FIG. 6.

With reference to FIG. 6, a series of different concentrations of the mcj plasmid ($Cm^R$) (dsDNA) (for example, 5, 10, 20 and 50 ng) was prepared to which the various components of the kit were added, including the primers at 125 ng/reaction. Lastly, 1 µl of PfuTurbo DNA polymerase was added and the reaction mixture was cycled in a PCR thermal cycler. The number of cycles depends on the procedure (e.g. 12 cycles for a point mutation; 16 for a single amino acid change, etc.). After this step, the reaction was cooled below 37° C. and 1 µl of Dpn I restriction enzyme was added to each reaction and incubated at 37° C. for 1 hr. This step is the key feature to the QuikChange kit, as Dpn I enzyme is specific to methylated and hemi-methylated DNA. As such, DpnI digests the parental DNA template but does not digest the mutant-synthesized DNA. As most *E. coli* strains produce methylated DNA, they are not resistant to Dpn I digestion. Undigested DNA was then used to transform DH5 α competent cells, and directly sequenced via high-throughput DNA sequencing using procedures well-known in the art. DH5 α cells are available, for example, from Invitrogen (Carlsbad, Calif.), which provides a protocol for transforming these cells. The cells were plated onto Cm agar plates for selection of the recombinants. Thereafter, high-throughput DNA sequencing of the recombinants was performed by Fidelity Systems, Inc. (Gaithersburg, Md.) according to the general procedure shown in FIG. 7.

Example 2

Biological Test for Mutant mcjA Activity

In the present example, the ability of an MccJ25 analog (mutant from Example 1) to inhibit growth of MccJ25-sensitive cells was assessed. It is noted that a similar procedure may be used with MccJ25-resistant cells, such as Gram-positive cells or cells that harbor mutations of the RNA polymerase secondary channel.

The MccJ25-sensitive cells may be D21T2TolC cells carrying a pRL663 plasmid, or other MccJ25-sensitive cells. Other suitable MccJ25-sensitive cells include, but are not limited to, DH10 β carrying a pRL663 plasmid or DH5 α cells carrying a pRL663 plasmid, which showed about the same level of sensitivity to MccJ25 as D21T2TolC, and were less temperature-sensitive.

Initially, LB broth including 200 µg/ml cloramphenicol was inoculated with cells (usually DH5 α cells) carrying a plasmid that produces a mutant MccJ25 from Example 1. The cultures were grown overnight at 37° C. These cultures were then spotted (2 µl) on an LB agar plate, which contained no antibiotic. The spots grew overnight (about 10 hours or more). Thereafter, the aforementioned MccJ25-sensitive cells (usually DH5 α cells carrying a pRL663 plasmid) were mixed with soft LB agar, and the mixture was poured over the grown spots. After incubation for about 5-8 hours at 37° C., cell growth inhibition zones could be seen.

For example, FIG. 5 shows a side view of a Petri dish containing two layers of agar. At the top surface of the bottom layer, cells harboring mutant MccJ25 are spotted and allowed to grow overnight, and the top layer contains the tester strain. Although the tester strain used in this example corresponds to wild-type, MccJ25-sensitive *E. coli*, other tester strains may be used, such as mutant, MccJ25-resistant cells with substitutions at various positions of the RNA polymerase secondary channel or MccJ25-resistant Gram-positive bacteria. The presence of a cell growth inhibition zone indicates the presence in the zone of cells producing an MccJ25 analog that inhibits growth of the tester cells (for e.g., the MccJ25-sensitive cells). As shown in FIG. 5, a cell growth inhibition zone corresponds to a clearance zone in the top agar layer which is located in an area including cells that produce an active MccJ25 analog.

As shown in FIG. 5, cells producing some MccJ25 mutants produced growth inhibition zones that were larger than those produced by wild-type MccJ25 cells, others produced zones that were equal to or smaller than the wild-type MccJ25-producing cells. Cells containing some mutant mcjA plasmids produced no inhibition zones. This can be due to the absence of mature MccJ25 production, failure of mutant MccJ25 to enter *E. coli*, or to inhibit RNA polymerase. In order to differentiate between these possibilities, Applicants performed the procedures described in Examples 3 and 4 below.

Example 3

Micropurification of MccJ25 Analogs and Screening of Purified MccJ25 Analogs by Mass Spectrometry (MALDI-MS)

Figure 8:
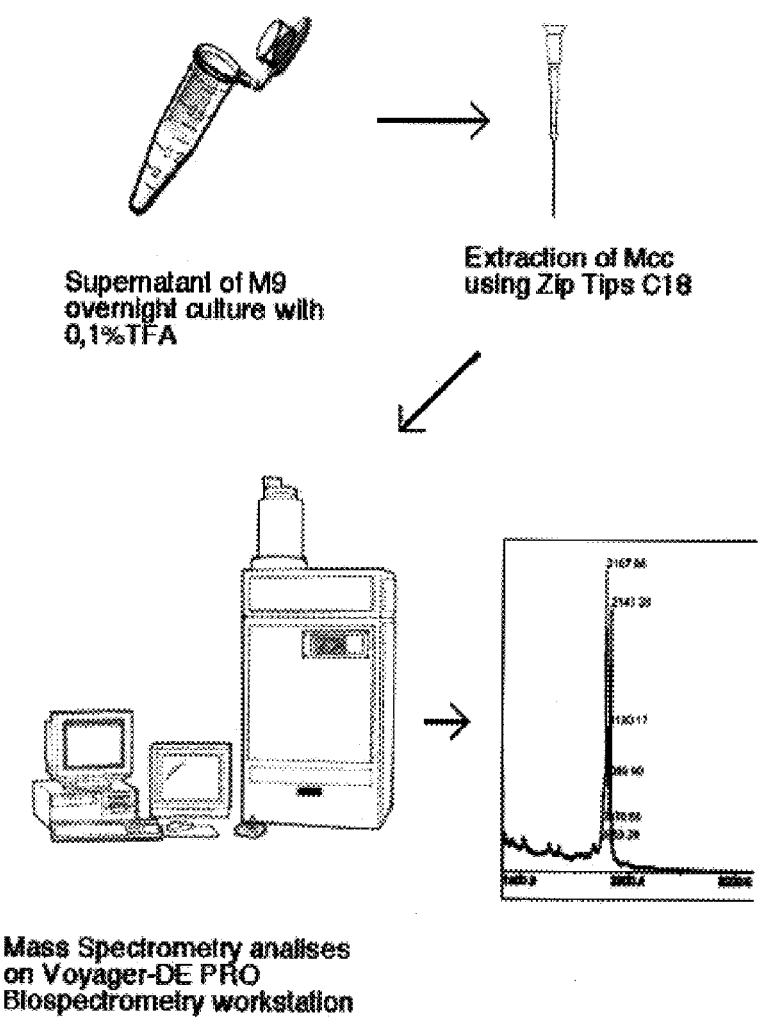
FIG. 8 illustrates screening of MccJ25 mutants by MALDI-MS.

In the present example, Applicants performed micropurification of mutant MccJ25 (i.e., the MccJ25 analogs) followed by mass spectral analysis to assess (1) mature MccJ25 analog production and (2) whether the MccJ25 analog matures into a threaded lasso structure characteristic of mature MccJ25. Wild-type MccJ25 was used as a control. With reference to FIG. 8, the MALDI-MS analysis used in the present example consists of two steps: sample preparation and mass spectral analysis. This is described in further detail below.

Applicants micropurified mutant MccJ25 or wild-type MccJ25 (control) from about 200 µl of cultured medium using $C_{18}$ ZipTips (Millipore Corporation). In particular, mutants (or control wt) were grown in overnight cultures at 37° C. in M9 media with 0.1% TFA. The overnight cultures were then centrifuged, and the supernatant was used for mutant MccJ25 purification using the $C_{18}$ ZipTips. The ZipTip was wetted with Solution A (AcOH 0.1%, Acetonitrile 95%) two times, using 10 µl each time. Then, the ZipTip was wetted with Solution B (0.1% AcOH) three times, using 10 µl each time. After the ZipTip had been wetted with Solution A and B as described, 100 µl of the supernatant including 0.1% Acetic Acid (AcOH) were added to the top of the ZipTip in aliquots of 10 µl. The ZipTip was then washed three times, 10 µl each time, with Solution A, and the MccJ25 mutant peptide was eluted with 5 µl of Solution C (50% Acetonitrile, 0.1% AcOH).

For the mass spectral analysis, 1 µl of the mutant MccJ25 sample prepared as described above was mixed with 1 µl of alpha-cyano-4-hydroxycinnamic acid. Then, 1 µl of the mixture was placed on a standard 100 spot plate. The mass spectral analysis was carried out on a Voyager-DE PRO Biospectrometry workstation. Representative mass-spectra are shown in FIG. 9, which shows mass spectra of the wild-type MccJ25 (SEQ ID NO:1), as well as mutants of MccJ25. The representative mutants shown include Ile13Ala (I13A), which is processed to yield a mature peptide and is active. This mutant is also referred to herein as [$Ala_{13}$]MccJ25 (SEQ ID NO:12). Also shown is Tyr20Phe (Y20F) (SEQ ID NO:37), which is processed to yield a mature peptide, but is inactive. Further shown is Tyr20Gly (Y20G) (SEQ ID NO:38), which is not processed into a mature peptide, and is inactive. Other representative mutants are shown in FIG. 1, some of which are processed into mature peptide, and have an activity level at least equal to or greater than wild-type mature MccJ25. These correspond to the black or red coded mutants, respectively, which appear above the MccJ25 wt sequence in FIG. 1.

Example 4

High-Throughput Transcription Assays

High-throughput transcription assays were performed by an adaptation of the fluorescence-detected-abortive-initiation assay method of Mukhopadhyay et al. 2004 (Mukhopadhyay, J., Sineva, E., Knight, J., Levy, R., and Ebright, R. (2004) Antibacterial peptide microcin J25 (MccJ25) inhibits transcription by binding within and obstructing the RNA polymerase secondary channel. *Mol. Cell.* 14, 739-751).

In particular, Assays were performed in Fluotrac-200 black, flat-bottom-well 96-well plates (Greiner Bio-One, Inc.). To each well, was added, successively, 43 µl culture supernatant (or 43 µl unmodified culture medium), 1 µl 5 µM *Escherichia coli* RNA polymerase holoenzyme (Epicentre, Inc.), 1 µl 1 µM DNA fragment lacUV5-12 (Mukhopadhyay, et al. (2001) *Cell* 106, 453-463), 1 µl 1 M Tris-HCl (pH 8.0), and 0.5 µl 1 M $MgCl_2$. Following 15 min at 37° C., 0.5 µl 1 mg/ml heparin (Sigma, Inc.) and 0.5 µl 2.5 mM (γ-AmNS) UTP (Molecular Probes, Inc.) were added. Following a further 2 min at 37° C., RNA synthesis was initiated by addition of 2.5 µl 10 mM $A_pA$ (Sigma, Inc.), and fluorescence emission intensity was monitored for 15 min at 37° C. [excitation wavelength=340 nm; emission wavelength=530 nm; excitation and emission band widths=20 nm; GENios Pro multimode scanner (TECAN)]. The quantity of UMP incorporated into RNA was determined from the quantity of (γ-AmNS) UTP consumed, which, in turn, was calculated as:

$$(\gamma\text{-}AmNS)UTP_{consumed} = [(\gamma\text{-}AmNS)UTP_0](F_t - F_0)/(12.4 \times F_0) \quad (1)$$

where $(\gamma\text{-}AmNS)UTP_0$ is the quantity of $(\gamma\text{-}AmNS)UTP$ at time 0, $F_0$ is the fluorescence emission intensity at time 0, and $F_t$ is the fluorescence emission intensity at time t. Quantities of UMP incorporated were compared for reaction mixtures containing culture supernatants and for control reaction mixtures containing unmodified culture medium.

FIG. 10 shows the comparison of transcription results obtained with wild-type MccJ25 (SEQ ID NO:1) and a MccJ25 mutant (MccJ25$^{TL}$; SEQ ID NO:39), which is inactive in vivo. At the top of FIG. 10, the growth of sensitive *E. coli* cells in microtiter plate wells containing the indicated concentrations of MccJ25 is shown. At the bottom of FIG. 10, results of in vitro transcription by wild-type RNA polymerase and MccJ25-resistant RNA Polymerase harboring the B' Thr931Ile mutation (T931I) in the presence of increasing concentrations of wild-type or mutant MccJ25$^{TL}$ are shown. The results show that even mutants which are biologically inactive, processed MccJ25 mutants (such as mutant MccJ25$^{TL}$) may still be able to bind to and inhibit in vitro the wild-type RNA polymerase, as well as MccJ25-resistant RNAP harboring mutations.

What is claimed is:

1. An analog of bacteriocidal peptide microcin J25 (MccJ25) that (1) has an amino acid sequence that differs from that of MccJ25 by having at least one amino acid substitution; and (2) that inhibits bacterial cell growth with a potency at least equal to that of MccJ25, wherein the analog is selected from the group consisting of [Ser$_3$] MccJ25 (SEQ ID NO:2), [Ile$_6$] MccJ25 (SEQ ID NO:3), [Phe$_6$] MccJ25 (SEQ ID NO:4), [Ala$_{11}$] MccJ25 (SEQ ID NO:5), [Trp$_{11}$] MccJ25 (SEQ ID NO:6), [Thr$_{12}$] MccJ25 (SEQ ID NO:7), [Ser$_{12}$] MccJ25 (SEQ ID NO:8), [Met$_{12}$] MccJ25 (SEQ ID NO:9), [His$_{12}$] MccJ25 (SEQ ID NO:10) [Leu$_{13}$] MccJ25 (SEQ ID NO:11), [Ala$_{13}$] MccJ25 (SEQ ID NO:12), [Asn$_{13}$] MccJ25 (SEQ ID NO:13 [Arg$_{13}$] MccJ25 (SEQ ID NO:14), [Pro$_{13}$] MccJ25 (SEQ ID NO:15), [Thr$_{13}$] MccJ25 (SEQ ID NO:16), [His$_{13}$] MccJ25 (SEQ ID NO:17), [Val$_{13}$] MccJ25

(SEQ ID NO:18), [Met$_{13}$] MccJ25 (SEQ ID NO:19), [Phe$_{13}$] MccJ25 (SEQ ID NO:20), [Trp$_{13}$] MccJ25 (SEQ ID NO:21), [Ser$_{14}$] MccJ25 (SEQ ID NO:22), [Thr$_{14}$] MccJ25 (SEQ ID NO:23), [Phe$_{15}$] MccJ25 (SEQ ID NO:24), [Gly$_{15}$] MccJ25 (SEQ ID NO:25), [Leu$_{15}$] MccJ25 (SEQ ID NO:26), [His$_{15}$] MccJ25 (SEQ ID NO:27), [Asn$_{15}$] MccJ25 (SEQ ID NO:28), [Ala$_{15}$] MccJ25 (SEQ ID NO:29), [Ile$_{15}$] MccJ25 (SEQ ID NO:30), [Trp$_{15}$] MccJ25 (SEQ ID NO:31), [Met$_{15}$] MccJ25 (SEQ ID NO:32), [Gln$_{16}$] MccJ25 (SEQ ID NO:33), [Glu$_{17}$] MccJ25 (SEQ ID NO:34), [Val$_{17}$] MccJ25 (SEQ ID NO:35) and combinations thereof.

2. The analog of claim 1, wherein the analog is selected from the group consisting of [Leu$_{13}$] MccJ25 (SEQ ID NO:11), [Ala$_{13}$] MccJ25 (SEQ ID NO:12), [Asn$_{13}$] MccJ25 (SEQ ID NO:13), [Arg$_{13}$] MccJ25 (SEQ ID NO:14), [Pro$_{13}$] MccJ25 (SEQ ID NO:15), [Thr$_{13}$] MccJ25 (SEQ ID NO:16), and [His$_{13}$] MccJ25 (SEQ ID NO:17).

3. The analog of claim 1, wherein the analog is selected from the group consisting of [Phe$_{15}$] MccJ25 (SEQ ID NO:24), [Gly$_{15}$] MccJ25 (SEQ ID NO:25), [Leu$_{15}$] MccJ25 (SEQ ID NO:26), [His$_{15}$] MccJ25 (SEQ ID NO:27), [Asn$_{15}$] MccJ25 (SEQ ID NO:28), [Ala$_{15}$] MccJ25 (SEQ ID NO:29) and [Ile$_{15}$] MccJ25 (SEQ ID NO:30).

4. The analog of claim 1, wherein the analog includes a detectable group.

5. The analog of claim 4, wherein the detectable group is selected from the group consisting of chromophores, fluorophores, and cyanine dyes.

6. The analog of claim 4, wherein the detectable group is located at a site of the amino acid substitution.

* * * * *

SEQUENCE LISTING

<160> NUMBER OF SEQ ID NOS: 39

<210> SEQ ID NO 1
<211> LENGTH: 21
<212> TYPE: PRT
<213> ORGANISM: Artificial sequence
<220> FEATURE:
<223> OTHER INFORMATION: synthetic peptide

<400> SEQUENCE: 1

Gly Gly Ala Gly His Val Pro Glu Tyr Phe Val Gly Ile Gly Thr Pro
1               5                   10                  15

Ile Ser Phe Tyr Gly
            20

<210> SEQ ID NO 2
<211> LENGTH: 21
<212> TYPE: PRT
<213> ORGANISM: Artificial sequence
<220> FEATURE:
<223> OTHER INFORMATION: synthetic peptide

<400> SEQUENCE: 2

Gly Gly Ser Gly His Val Pro Glu Tyr Phe Val Gly Ile Gly Thr Pro
1               5                   10                  15

Ile Ser Phe Tyr Gly
            20

<210> SEQ ID NO 3
<211> LENGTH: 21
<212> TYPE: PRT
<213> ORGANISM: Artificial sequence
<220> FEATURE:
<223> OTHER INFORMATION: synthetic peptide

<400> SEQUENCE: 3

Gly Gly Ala Gly His Ile Pro Glu Tyr Phe Val Gly Ile Gly Thr Pro
1               5                   10                  15

Ile Ser Phe Tyr Gly
            20

<210> SEQ ID NO 4
<211> LENGTH: 21
<212> TYPE: PRT
<213> ORGANISM: Artificial sequence
<220> FEATURE:
<223> OTHER INFORMATION: synthetic peptide

<400> SEQUENCE: 4

Gly Gly Ala Gly His Phe Pro Glu Tyr Phe Val Gly Ile Gly Thr Pro
1               5                   10                  15

Ile Ser Phe Tyr Gly
            20

<210> SEQ ID NO 5
<211> LENGTH: 21
<212> TYPE: PRT
<213> ORGANISM: Artificial sequence
<220> FEATURE:
<223> OTHER INFORMATION: synthetic peptide

<400> SEQUENCE: 5

Gly Gly Ala Gly His Val Pro Glu Tyr Phe Ala Gly Ile Gly Thr Pro
1               5                   10                  15

Ile Ser Phe Tyr Gly
            20

<210> SEQ ID NO 6
<211> LENGTH: 21
<212> TYPE: PRT
<213> ORGANISM: Artificial sequence
<220> FEATURE:
<223> OTHER INFORMATION: synthetic peptide

<400> SEQUENCE: 6

Gly Gly Ala Gly His Val Pro Glu Tyr Phe Trp Gly Ile Gly Thr Pro
1               5                   10                  15

Ile Ser Phe Tyr Gly
            20

<210> SEQ ID NO 7
<211> LENGTH: 21
<212> TYPE: PRT
<213> ORGANISM: Artificial sequence
<220> FEATURE:
<223> OTHER INFORMATION: synthetic peptide

<400> SEQUENCE: 7

Gly Gly Ala Gly His Val Pro Glu Tyr Phe Val Thr Ile Gly Thr Pro
1               5                   10                  15

Ile Ser Phe Tyr Gly
            20

<210> SEQ ID NO 8
<211> LENGTH: 21
<212> TYPE: PRT
<213> ORGANISM: Artificial sequence
<220> FEATURE:
<223> OTHER INFORMATION: synthetic peptide

<400> SEQUENCE: 8

Gly Gly Ala Gly His Val Pro Glu Tyr Phe Val Ser Ile Gly Thr Pro
1               5                   10                  15

Ile Ser Phe Tyr Gly
            20

<210> SEQ ID NO 9
<211> LENGTH: 21
<212> TYPE: PRT
<213> ORGANISM: Artificial sequence
<220> FEATURE:
<223> OTHER INFORMATION: synthetic peptide

<400> SEQUENCE: 9

Gly Gly Ala Gly His Val Pro Glu Tyr Phe Val Met Ile Gly Thr Pro
1               5                   10                  15

Ile Ser Phe Tyr Gly
            20

<210> SEQ ID NO 10
<211> LENGTH: 21
<212> TYPE: PRT
<213> ORGANISM: Artificial sequence
<220> FEATURE:
<223> OTHER INFORMATION: synthetic peptide

<400> SEQUENCE: 10

Gly Gly Ala Gly His Val Pro Glu Tyr Phe Val His Ile Gly Thr Pro
1               5                   10                  15

Ile Ser Phe Tyr Gly
            20

<210> SEQ ID NO 11
<211> LENGTH: 21
<212> TYPE: PRT
<213> ORGANISM: Artificial sequence
<220> FEATURE:
<223> OTHER INFORMATION: synthetic peptide

<400> SEQUENCE: 11

Gly Gly Ala Gly His Val Pro Glu Tyr Phe Val Gly Leu Gly Thr Pro
1               5                   10                  15

Ile Ser Phe Tyr Gly
            20

<210> SEQ ID NO 12
<211> LENGTH: 21
<212> TYPE: PRT
<213> ORGANISM: Artificial sequence
<220> FEATURE:
<223> OTHER INFORMATION: synthetic peptide

<400> SEQUENCE: 12

Gly Gly Ala Gly His Val Pro Glu Tyr Phe Val Gly Ala Gly Thr Pro
1               5                   10                  15

Ile Ser Phe Tyr Gly
            20

<210> SEQ ID NO 13
<211> LENGTH: 21
<212> TYPE: PRT
<213> ORGANISM: Artificial sequence
<220> FEATURE:
<223> OTHER INFORMATION: synthetic peptide

<400> SEQUENCE: 13

Gly Gly Ala Gly His Val Pro Glu Tyr Phe Val Gly Asn Gly Thr Pro
1               5                   10                  15

Ile Ser Phe Tyr Gly
            20

<210> SEQ ID NO 14
<211> LENGTH: 21
<212> TYPE: PRT
<213> ORGANISM: Artificial sequence
<220> FEATURE:
<223> OTHER INFORMATION: synthetic peptide

<400> SEQUENCE: 14

Gly Gly Ala Gly His Val Pro Glu Tyr Phe Val Gly Arg Gly Thr Pro
1               5                   10                  15

Ile Ser Phe Tyr Gly
            20

<210> SEQ ID NO 15
<211> LENGTH: 21
<212> TYPE: PRT
<213> ORGANISM: Artificial sequence
<220> FEATURE:
<223> OTHER INFORMATION: synthetic peptide

<400> SEQUENCE: 15

Gly Gly Ala Gly His Val Pro Glu Tyr Phe Val Gly Pro Gly Thr Pro
1               5                   10                  15

Ile Ser Phe Tyr Gly
            20

<210> SEQ ID NO 16
<211> LENGTH: 21
<212> TYPE: PRT
<213> ORGANISM: Artificial sequence
<220> FEATURE:

```
<223> OTHER INFORMATION: synthetic peptide

<400> SEQUENCE: 16

Gly Gly Ala Gly His Val Pro Glu Tyr Phe Val Gly Thr Gly Thr Pro
 1               5                  10                  15

Ile Ser Phe Tyr Gly
            20

<210> SEQ ID NO 17
<211> LENGTH: 21
<212> TYPE: PRT
<213> ORGANISM: Artificial sequence
<220> FEATURE:
<223> OTHER INFORMATION: synthetic peptide

<400> SEQUENCE: 17

Gly Gly Ala Gly His Val Pro Glu Tyr Phe Val Gly His Gly Thr Pro
 1               5                  10                  15

Ile Ser Phe Tyr Gly
            20

<210> SEQ ID NO 18
<211> LENGTH: 21
<212> TYPE: PRT
<213> ORGANISM: Artificial sequence
<220> FEATURE:
<223> OTHER INFORMATION: synthetic peptide

<400> SEQUENCE: 18

Gly Gly Ala Gly His Val Pro Glu Tyr Phe Val Gly Val Gly Thr Pro
 1               5                  10                  15

Ile Ser Phe Tyr Gly
            20

<210> SEQ ID NO 19
<211> LENGTH: 21
<212> TYPE: PRT
<213> ORGANISM: Artificial sequence
<220> FEATURE:
<223> OTHER INFORMATION: synthetic peptide

<400> SEQUENCE: 19

Gly Gly Ala Gly His Val Pro Glu Tyr Phe Val Gly Met Gly Thr Pro
 1               5                  10                  15

Ile Ser Phe Tyr Gly
            20

<210> SEQ ID NO 20
<211> LENGTH: 21
<212> TYPE: PRT
<213> ORGANISM: Artificial sequence
<220> FEATURE:
<223> OTHER INFORMATION: synthetic peptide

<400> SEQUENCE: 20

Gly Gly Ala Gly His Val Pro Glu Tyr Phe Val Gly Phe Gly Thr Pro
 1               5                  10                  15

Ile Ser Phe Tyr Gly
            20

<210> SEQ ID NO 21
<211> LENGTH: 21
<212> TYPE: PRT
<213> ORGANISM: Artificial sequence
```

```
<220> FEATURE:
<223> OTHER INFORMATION: synthetic peptide

<400> SEQUENCE: 21

Gly Gly Ala Gly His Val Pro Glu Tyr Phe Val Gly Trp Gly Thr Pro
1               5                   10                  15

Ile Ser Phe Tyr Gly
            20

<210> SEQ ID NO 22
<211> LENGTH: 21
<212> TYPE: PRT
<213> ORGANISM: Artificial sequence
<220> FEATURE:
<223> OTHER INFORMATION: synthetic peptide

<400> SEQUENCE: 22

Gly Gly Ala Gly His Val Pro Glu Tyr Phe Val Gly Ile Ser Thr Pro
1               5                   10                  15

Ile Ser Phe Tyr Gly
            20

<210> SEQ ID NO 23
<211> LENGTH: 21
<212> TYPE: PRT
<213> ORGANISM: Artificial sequence
<220> FEATURE:
<223> OTHER INFORMATION: synthetic peptide

<400> SEQUENCE: 23

Gly Gly Ala Gly His Val Pro Glu Tyr Phe Val Gly Ile Thr Thr Pro
1               5                   10                  15

Ile Ser Phe Tyr Gly
            20

<210> SEQ ID NO 24
<211> LENGTH: 21
<212> TYPE: PRT
<213> ORGANISM: Artificial sequence
<220> FEATURE:
<223> OTHER INFORMATION: synthetic peptide

<400> SEQUENCE: 24

Gly Gly Ala Gly His Val Pro Glu Tyr Phe Val Gly Ile Gly Phe Pro
1               5                   10                  15

Ile Ser Phe Tyr Gly
            20

<210> SEQ ID NO 25
<211> LENGTH: 21
<212> TYPE: PRT
<213> ORGANISM: Artificial sequence
<220> FEATURE:
<223> OTHER INFORMATION: synthetic peptide

<400> SEQUENCE: 25

Gly Gly Ala Gly His Val Pro Glu Tyr Phe Val Gly Ile Gly Gly Pro
1               5                   10                  15

Ile Ser Phe Tyr Gly
            20

<210> SEQ ID NO 26
<211> LENGTH: 21
<212> TYPE: PRT
```

<213> ORGANISM: Artificial sequence
<220> FEATURE:
<223> OTHER INFORMATION: synthetic peptide

<400> SEQUENCE: 26

Gly Gly Ala Gly His Val Pro Glu Tyr Phe Val Gly Ile Gly Leu Pro
1               5                   10                  15

Ile Ser Phe Tyr Gly
            20

<210> SEQ ID NO 27
<211> LENGTH: 21
<212> TYPE: PRT
<213> ORGANISM: Artificial sequence
<220> FEATURE:
<223> OTHER INFORMATION: synthetic peptide

<400> SEQUENCE: 27

Gly Gly Ala Gly His Val Pro Glu Tyr Phe Val Gly Ile Gly His Pro
1               5                   10                  15

Ile Ser Phe Tyr Gly
            20

<210> SEQ ID NO 28
<211> LENGTH: 21
<212> TYPE: PRT
<213> ORGANISM: Artificial sequence
<220> FEATURE:
<223> OTHER INFORMATION: synthetic peptide

<400> SEQUENCE: 28

Gly Gly Ala Gly His Val Pro Glu Tyr Phe Val Gly Ile Gly Asn Pro
1               5                   10                  15

Ile Ser Phe Tyr Gly
            20

<210> SEQ ID NO 29
<211> LENGTH: 21
<212> TYPE: PRT
<213> ORGANISM: Artificial sequence
<220> FEATURE:
<223> OTHER INFORMATION: synthetic peptide

<400> SEQUENCE: 29

Gly Gly Ala Gly His Val Pro Glu Tyr Phe Val Gly Ile Gly Ala Pro
1               5                   10                  15

Ile Ser Phe Tyr Gly
            20

<210> SEQ ID NO 30
<211> LENGTH: 21
<212> TYPE: PRT
<213> ORGANISM: Artificial sequence
<220> FEATURE:
<223> OTHER INFORMATION: synthetic peptide

<400> SEQUENCE: 30

Gly Gly Ala Gly His Val Pro Glu Tyr Phe Val Gly Ile Gly Ile Pro
1               5                   10                  15

Ile Ser Phe Tyr Gly
            20

<210> SEQ ID NO 31
<211> LENGTH: 21

```
<212> TYPE: PRT
<213> ORGANISM: Artificial sequence
<220> FEATURE:
<223> OTHER INFORMATION: synthetic peptide

<400> SEQUENCE: 31

Gly Gly Ala Gly His Val Pro Glu Tyr Phe Val Gly Ile Gly Trp Pro
1               5                   10                  15

Ile Ser Phe Tyr Gly
            20

<210> SEQ ID NO 32
<211> LENGTH: 21
<212> TYPE: PRT
<213> ORGANISM: Artificial sequence
<220> FEATURE:
<223> OTHER INFORMATION: synthetic peptide

<400> SEQUENCE: 32

Gly Gly Ala Gly His Val Pro Glu Tyr Phe Val Gly Ile Gly Met Pro
1               5                   10                  15

Ile Ser Phe Tyr Gly
            20

<210> SEQ ID NO 33
<211> LENGTH: 21
<212> TYPE: PRT
<213> ORGANISM: Artificial sequence
<220> FEATURE:
<223> OTHER INFORMATION: synthetic peptide

<400> SEQUENCE: 33

Gly Gly Ala Gly His Val Pro Glu Tyr Phe Val Gly Ile Gly Thr Gln
1               5                   10                  15

Ile Ser Phe Tyr Gly
            20

<210> SEQ ID NO 34
<211> LENGTH: 21
<212> TYPE: PRT
<213> ORGANISM: Artificial sequence
<220> FEATURE:
<223> OTHER INFORMATION: synthetic peptide

<400> SEQUENCE: 34

Gly Gly Ala Gly His Val Pro Glu Tyr Phe Val Gly Ile Gly Thr Pro
1               5                   10                  15

Glu Ser Phe Tyr Gly
            20

<210> SEQ ID NO 35
<211> LENGTH: 21
<212> TYPE: PRT
<213> ORGANISM: Artificial sequence
<220> FEATURE:
<223> OTHER INFORMATION: synthetic peptide

<400> SEQUENCE: 35

Gly Gly Ala Gly His Val Pro Glu Tyr Phe Val Gly Ile Gly Thr Pro
1               5                   10                  15

Val Ser Phe Tyr Gly
            20

<210> SEQ ID NO 36
```

```
<211> LENGTH: 58
<212> TYPE: PRT
<213> ORGANISM: Artificial sequence
<220> FEATURE:
<223> OTHER INFORMATION: synthetic peptide

<400> SEQUENCE: 36

Met Ile Lys His Phe His Phe Asn Lys Leu Ser Ser Gly Lys Lys Asn
1               5                   10                  15

Asn Val Pro Ser Pro Ala Lys Gly Val Ile Gln Ile Lys Lys Ser Ala
            20                  25                  30

Ser Gln Leu Thr Lys Gly Gly Ala Gly His Val Pro Glu Tyr Phe Val
        35                  40                  45

Gly Ile Gly Thr Pro Ile Ser Phe Tyr Gly
    50                  55

<210> SEQ ID NO 37
<211> LENGTH: 21
<212> TYPE: PRT
<213> ORGANISM: Artificial sequence
<220> FEATURE:
<223> OTHER INFORMATION: synthetic peptide

<400> SEQUENCE: 37

Gly Gly Ala Gly His Val Pro Glu Tyr Phe Val Gly Ile Gly Thr Pro
1               5                   10                  15

Ile Ser Phe Phe Gly
            20

<210> SEQ ID NO 38
<211> LENGTH: 21
<212> TYPE: PRT
<213> ORGANISM: Artificial sequence
<220> FEATURE:
<223> OTHER INFORMATION: synthetic peptide

<400> SEQUENCE: 38

Gly Gly Ala Gly His Val Pro Glu Tyr Phe Val Gly Ile Gly Thr Pro
1               5                   10                  15

Ile Ser Phe Gly Gly
            20

<210> SEQ ID NO 39
<211> LENGTH: 21
<212> TYPE: PRT
<213> ORGANISM: Artificial sequence
<220> FEATURE:
<223> OTHER INFORMATION: synthetic peptide

<400> SEQUENCE: 39

Gly Gly Ala Gly His Val Pro Glu Tyr Phe Val Gly Ile Gly Leu Pro
1               5                   10                  15

Ile Ser Phe Tyr Gly
            20
```